United States Patent
Ben-Ezra et al.

(10) Patent No.: US 8,571,651 B2
(45) Date of Patent: Oct. 29, 2013

(54) TECHNIQUES FOR REDUCING PAIN ASSOCIATED WITH NERVE STIMULATION

(75) Inventors: Omry Ben-Ezra, Jerusalem (IL); Tamir Ben-David, Tel Aviv (IL); Ehud Cohen, Ganei Tikva (IL)

(73) Assignee: Bio Control Medical (B.C.M.) Ltd., Yehud (IL)

( * ) Notice: Subject to any disclaimer, the term of this patent is extended or adjusted under 35 U.S.C. 154(b) by 0 days.

(21) Appl. No.: 13/022,199

(22) Filed: Feb. 7, 2011

(65) Prior Publication Data

US 2011/0137365 A1 Jun. 9, 2011

Related U.S. Application Data

(62) Division of application No. 11/517,888, filed on Sep. 7, 2006, now Pat. No. 7,904,176.

(51) Int. Cl.
*A61N 1/36* (2006.01)
(52) U.S. Cl.
USPC .................................................. 607/2
(58) Field of Classification Search
USPC ............................................ 607/2, 116, 118
See application file for complete search history.

(56) References Cited

U.S. PATENT DOCUMENTS

| 3,411,507 A | 11/1968 | Wingrove |
| 3,952,750 A | 4/1976 | Mirowski |
| 4,019,518 A | 4/1977 | Maurer |
| 4,161,952 A | 7/1979 | Heilman |
| 4,338,945 A | 7/1982 | Kosugi |

(Continued)

FOREIGN PATENT DOCUMENTS

| EP | 0688577 | 12/1995 |
| EP | 0831954 | 4/1998 |

(Continued)

OTHER PUBLICATIONS

Akselrod S et al., "Power spectrum analysis of heart rate fluctuation: a quantitative probe of beat-to-beat cardiovascular control," Science 213: 220-222 (1981).

(Continued)

*Primary Examiner* — Amanda Patton
(74) *Attorney, Agent, or Firm* — Sughrue Mion, PLLC

(57) ABSTRACT

Apparatus is provided including an electrode device and a control unit. The electrode device is configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein. The control unit is configured to drive the electrode device to apply to the site a current in at least first and second bursts, the first burst including a plurality of pulses, and the second burst including at least one pulse, and set (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval between, the percentage being less than 67%. Other embodiments are also described.

39 Claims, 7 Drawing Sheets

(56) References Cited

U.S. PATENT DOCUMENTS

| | | |
|---|---|---|
| 4,392,496 A | 7/1983 | Stanton |
| 4,535,785 A | 8/1985 | Honert |
| 4,559,948 A | 12/1985 | Liss |
| 4,573,481 A | 3/1986 | Bullara |
| 4,585,005 A | 4/1986 | Lue |
| 4,602,624 A | 7/1986 | Naples |
| 4,608,985 A | 9/1986 | Crish |
| 4,628,942 A | 12/1986 | Sweeney |
| 4,632,116 A | 12/1986 | Rosen |
| 4,649,936 A | 3/1987 | Ungar |
| 4,663,102 A | 5/1987 | Brenman |
| 4,702,254 A | 10/1987 | Zabara |
| 4,739,764 A | 4/1988 | Lue |
| 4,867,164 A | 9/1989 | Zabara |
| 4,922,908 A | 5/1990 | Morawetz |
| 4,926,865 A | 5/1990 | Oman |
| 4,962,751 A | 10/1990 | Krauter |
| 5,025,807 A | 6/1991 | Zabara |
| 5,042,497 A | 8/1991 | Shapland |
| 5,069,680 A | 12/1991 | Grandjean |
| 5,095,905 A | 3/1992 | Klepinski |
| 5,143,067 A | 9/1992 | Rise et al. |
| 5,170,802 A | 12/1992 | Mehra |
| 5,178,616 A | 1/1993 | Uemiya |
| 5,188,104 A | 2/1993 | Wernicke |
| 5,199,428 A | 4/1993 | Obel |
| 5,199,430 A | 4/1993 | Fang |
| 5,203,326 A | 4/1993 | Collins |
| 5,205,258 A | 4/1993 | Hashimoto |
| 5,205,285 A | 4/1993 | Baker, Jr. |
| 5,215,086 A | 6/1993 | Terry, Jr. |
| 5,224,491 A | 7/1993 | Mehra |
| 5,243,980 A | 9/1993 | Mehra |
| 5,251,621 A | 10/1993 | Collins |
| 5,263,480 A | 11/1993 | Wernicke |
| 5,282,468 A | 2/1994 | Klepinski |
| 5,292,344 A | 3/1994 | Douglas |
| 5,299,569 A | 4/1994 | Wernicke |
| 5,314,495 A | 5/1994 | Kovacs |
| 5,330,507 A | 7/1994 | Schwartz |
| 5,334,221 A | 8/1994 | Bardy |
| 5,335,657 A | 8/1994 | Terry, Jr. |
| 5,344,438 A | 9/1994 | Testerman et al. |
| 5,356,425 A | 10/1994 | Bardy |
| 5,411,531 A | 5/1995 | Hill |
| 5,423,872 A | 6/1995 | Cigaina |
| 5,437,285 A | 8/1995 | Verrier |
| 5,439,938 A | 8/1995 | Snyder |
| 5,454,840 A | 10/1995 | Krakovsky |
| 5,507,784 A | 4/1996 | Hill |
| 5,522,854 A | 6/1996 | Ideker |
| 5,540,730 A | 7/1996 | Terry, Jr. |
| 5,540,734 A | 7/1996 | Zabara |
| 5,562,718 A | 10/1996 | Palermo |
| 5,571,150 A | 11/1996 | Wernicke |
| 5,575,766 A | 11/1996 | Swartz |
| 5,578,061 A | 11/1996 | Stroetmann |
| 5,602,301 A | 2/1997 | Field |
| 5,634,462 A | 6/1997 | Tyler |
| 5,645,570 A | 7/1997 | Corbucci |
| 5,658,318 A | 8/1997 | Stroetmann |
| 5,662,689 A | 9/1997 | Elsberry |
| 5,690,681 A | 11/1997 | Geddes |
| 5,690,691 A | 11/1997 | Chen |
| 5,700,282 A | 12/1997 | Zabara |
| 5,707,400 A | 1/1998 | Terry, Jr. |
| 5,711,316 A | 1/1998 | Elsberry |
| 5,716,385 A | 2/1998 | Mittal |
| 5,755,750 A | 5/1998 | Petruska |
| 5,824,027 A | 10/1998 | Hoffer |
| 5,832,932 A | 11/1998 | Elsberry |
| 5,833,709 A | 11/1998 | Rise |
| 5,836,994 A | 11/1998 | Bourgeois |
| 5,891,179 A | 4/1999 | Er |
| 5,916,239 A | 6/1999 | Geddes |
| 5,928,269 A | 7/1999 | Alt |
| 5,938,584 A | 8/1999 | Ardito |
| 6,006,134 A | 12/1999 | Hill |
| 6,026,326 A | 2/2000 | Bardy |
| 6,038,476 A | 3/2000 | Schwartz |
| 6,058,331 A | 5/2000 | King |
| 6,066,163 A | 5/2000 | John |
| 6,073,048 A | 6/2000 | Kieval |
| 6,083,249 A | 7/2000 | Familoni |
| 6,086,525 A | 7/2000 | Davey |
| 6,091,977 A | 7/2000 | Tarjan |
| 6,091,992 A | 7/2000 | Bourgeois |
| 6,094,598 A | 7/2000 | Elsberry |
| 6,097,984 A | 8/2000 | Douglas |
| 6,104,955 A | 8/2000 | Bourgeois |
| 6,104,960 A | 8/2000 | Duysens |
| 6,119,516 A | 9/2000 | Hock |
| 6,134,470 A | 10/2000 | Hartlaub |
| 6,146,335 A | 11/2000 | Gozani |
| 6,161,029 A | 12/2000 | Spreigl |
| 6,167,304 A | 12/2000 | Loos |
| 6,169,924 B1 | 1/2001 | Meloy |
| 6,178,349 B1 | 1/2001 | Kieval |
| 6,205,359 B1 | 3/2001 | Boveja |
| 6,230,061 B1 | 5/2001 | Hartung |
| 6,240,314 B1 | 5/2001 | Plicchi |
| 6,256,537 B1 | 7/2001 | Stoop |
| 6,266,564 B1 | 7/2001 | Hill |
| 6,272,377 B1 | 8/2001 | Sweeney |
| 6,292,695 B1 | 9/2001 | Webster, Jr. |
| 6,308,105 B1 | 10/2001 | Duysens et al. |
| 6,319,241 B1 | 11/2001 | King |
| 6,341,236 B1 | 1/2002 | Osorio |
| 6,356,784 B1 | 3/2002 | Lozano |
| 6,366,813 B1 | 4/2002 | DiLorenzo |
| 6,381,499 B1 | 4/2002 | Taylor |
| 6,393,323 B1 | 5/2002 | Sawan |
| 6,400,982 B2 | 6/2002 | Sweeney |
| 6,405,079 B1 | 6/2002 | Ansarinia |
| 6,434,424 B1 | 8/2002 | Igel |
| 6,449,507 B1 | 9/2002 | Hill |
| 6,463,382 B1 | 10/2002 | Bullock |
| 6,473,644 B1 | 10/2002 | Terry, Jr. |
| 6,493,585 B2 | 12/2002 | Plicchi |
| 6,511,500 B1 | 1/2003 | Rahme |
| 6,522,926 B1 | 2/2003 | Kieval |
| 6,542,774 B2 | 4/2003 | Hill |
| 6,564,096 B2 | 5/2003 | Mest |
| 6,571,121 B2 | 5/2003 | Schroeppel |
| 6,571,122 B2 | 5/2003 | Schroeppel |
| 6,587,727 B2 | 7/2003 | Osorio |
| 6,600,954 B2 | 7/2003 | Cohen |
| 6,600,956 B2 | 7/2003 | Maschino |
| 6,605,447 B2 | 8/2003 | Weiss |
| 6,610,713 B2 | 8/2003 | Tracey |
| 6,620,186 B2 | 9/2003 | Saphon |
| 6,622,041 B2 | 9/2003 | Terry, Jr. |
| 6,628,987 B1 | 9/2003 | Hill |
| 6,668,191 B1 | 12/2003 | Boveja |
| 6,671,556 B2 | 12/2003 | Osorio |
| 6,684,105 B2 | 1/2004 | Cohen |
| 6,839,594 B2 | 1/2005 | Cohen |
| RE38,705 E | 2/2005 | Hill |
| 6,865,416 B2 | 3/2005 | Dev |
| 6,866,657 B2 | 3/2005 | Shchervinsky |
| 6,885,888 B2 | 4/2005 | Rezai |
| 6,892,098 B2 | 5/2005 | Ayal |
| 6,895,280 B2 | 5/2005 | Meadows |
| 6,907,293 B2 | 6/2005 | Grill |
| 6,907,295 B2 | 6/2005 | Gross |
| 6,928,320 B2 | 8/2005 | King |
| 6,934,583 B2 | 8/2005 | Weinberg |
| 6,985,774 B2 | 1/2006 | Kieval |
| 7,050,846 B2 | 5/2006 | Sweeney |
| 7,076,299 B2 | 7/2006 | Thong |
| 7,076,307 B2 | 7/2006 | Boveja |
| 7,079,891 B1 | 7/2006 | Kroll |
| 7,113,816 B2 | 9/2006 | Matsukawa et al. |
| 7,123,961 B1 | 10/2006 | Kroll |

(56) References Cited

U.S. PATENT DOCUMENTS

| | | |
|---|---|---|
| 7,136,700 B1 | 11/2006 | Province |
| 7,142,917 B2 | 11/2006 | Fukui |
| 7,225,016 B1 | 5/2007 | Koh |
| 7,248,930 B1 | 7/2007 | Woloszko et al. |
| 7,295,881 B2 | 11/2007 | Cohen |
| 7,321,793 B2 | 1/2008 | Ben Ezra |
| 7,403,819 B1 | 7/2008 | Shelchuk |
| 7,460,906 B2 | 12/2008 | Libbus |
| 7,509,166 B2 | 3/2009 | Libbus |
| 7,561,922 B2 | 7/2009 | Cohen |
| 7,584,004 B2 | 9/2009 | Caparso et al. |
| 7,623,926 B2 | 11/2009 | Rossing |
| 7,627,384 B2 | 12/2009 | Ayal |
| 7,634,317 B2 | 12/2009 | Ben-David |
| 7,668,602 B2 | 2/2010 | Ben-David |
| 7,734,355 B2 | 6/2010 | Cohen |
| 7,749,900 B2 | 7/2010 | Li |
| 7,765,000 B2 | 7/2010 | Zhang |
| 7,778,703 B2 | 8/2010 | Gross |
| 7,778,711 B2 | 8/2010 | Ben-David |
| 7,809,442 B2 | 10/2010 | Bolea et al. |
| 7,844,346 B2 | 11/2010 | Cohen |
| 7,885,709 B2 | 2/2011 | Ben-David |
| 7,885,711 B2 | 2/2011 | Ben-Ezra |
| 7,890,185 B2 | 2/2011 | Cohen |
| 7,904,176 B2 | 3/2011 | Ben-Ezra |
| 7,974,693 B2 | 7/2011 | Ben-David |
| 7,996,092 B2 | 8/2011 | Mrva et al. |
| 8,005,542 B2 | 8/2011 | Ben-Ezra |
| 8,155,757 B1 | 4/2012 | Neisz et al. |
| 8,214,056 B2 | 7/2012 | Hoffer et al. |
| 8,224,444 B2 | 7/2012 | Ben-David |
| 2001/0003799 A1 | 6/2001 | Boveja |
| 2002/0016344 A1 | 2/2002 | Tracey |
| 2002/0029002 A1 | 3/2002 | Bardy |
| 2002/0035335 A1 | 3/2002 | Schauerte |
| 2002/0055761 A1 | 5/2002 | Mann |
| 2002/0099419 A1 | 7/2002 | Cohen |
| 2002/0107553 A1 | 8/2002 | Hill |
| 2002/0120304 A1 | 8/2002 | Mest |
| 2002/0161415 A1 | 10/2002 | Cohen |
| 2003/0027794 A1 | 2/2003 | Arnaiz |
| 2003/0040774 A1 | 2/2003 | Terry, Jr. |
| 2003/0045909 A1 | 3/2003 | Gross |
| 2003/0045914 A1 | 3/2003 | Cohen |
| 2003/0050677 A1 | 3/2003 | Gross |
| 2003/0078623 A1 | 4/2003 | Weinberg |
| 2003/0100933 A1 | 5/2003 | Ayal |
| 2003/0144709 A1 | 7/2003 | Zabara |
| 2003/0195574 A1 | 10/2003 | Osorio |
| 2003/0212440 A1 | 11/2003 | Boveja |
| 2003/0216775 A1 | 11/2003 | Hill |
| 2003/0229380 A1 | 12/2003 | Adams |
| 2003/0233129 A1 | 12/2003 | Matos |
| 2003/0236557 A1 | 12/2003 | Whitehurst |
| 2004/0002740 A1 | 1/2004 | Lee |
| 2004/0006311 A1 | 1/2004 | Shchervinsky |
| 2004/0006331 A1 | 1/2004 | Shchervinsky |
| 2004/0048795 A1 | 3/2004 | Ivanova |
| 2004/0138721 A1 | 7/2004 | Osorio |
| 2004/0152958 A1 | 8/2004 | Frei |
| 2004/0158119 A1 | 8/2004 | Osorio |
| 2004/0162594 A1 | 8/2004 | King |
| 2004/0172075 A1 | 9/2004 | Shafer |
| 2004/0172094 A1 | 9/2004 | Cohen |
| 2004/0193231 A1 | 9/2004 | Ben-David |
| 2004/0199210 A1 | 10/2004 | Shelchuk |
| 2004/0215087 A1 | 10/2004 | Genero |
| 2004/0215289 A1 | 10/2004 | Fukui |
| 2004/0243182 A1 | 12/2004 | Cohen |
| 2004/0249416 A1 | 12/2004 | Yun |
| 2004/0254612 A1 | 12/2004 | Ezra |
| 2005/0010265 A1 | 1/2005 | Baru et al. |
| 2005/0065553 A1 | 3/2005 | Ben Ezra |
| 2005/0119704 A1 | 6/2005 | Peters et al. |
| 2005/0125044 A1 | 6/2005 | Tracey |
| 2005/0131467 A1 | 6/2005 | Boveja |
| 2005/0143787 A1 | 6/2005 | Boveja |
| 2005/0149154 A1 | 7/2005 | Cohen |
| 2005/0187584 A1 | 8/2005 | Denker |
| 2005/0187586 A1 | 8/2005 | Ben-David |
| 2005/0197675 A1* | 9/2005 | David et al. ................ 607/9 |
| 2005/0222644 A1 | 10/2005 | Killan |
| 2005/0267542 A1 | 12/2005 | Ben-David |
| 2006/0015153 A1 | 1/2006 | Gliner |
| 2006/0047213 A1 | 3/2006 | Gavriely et al. |
| 2006/0052831 A1 | 3/2006 | Fukui |
| 2006/0074450 A1 | 4/2006 | Boveja |
| 2006/0100668 A1 | 5/2006 | Ben-David |
| 2006/0106441 A1 | 5/2006 | Ayal |
| 2006/0116739 A1 | 6/2006 | Betser |
| 2006/0129205 A1 | 6/2006 | Boveja |
| 2006/0136024 A1 | 6/2006 | Cohen |
| 2006/0149339 A1 | 7/2006 | Burnes |
| 2006/0167498 A1 | 7/2006 | DiLorenzo |
| 2006/0167501 A1 | 7/2006 | Ben-David |
| 2006/0195170 A1 | 8/2006 | Cohen |
| 2006/0206155 A1 | 9/2006 | Ben-David |
| 2006/0259077 A1 | 11/2006 | Pardo |
| 2006/0265027 A1 | 11/2006 | Vaingast |
| 2006/0271115 A1 | 11/2006 | Ben-Ezra |
| 2006/0271137 A1 | 11/2006 | Stanton-Hicks |
| 2006/0282145 A1 | 12/2006 | Caparso et al. |
| 2007/0021786 A1 | 1/2007 | Parnis |
| 2007/0027487 A1 | 2/2007 | Mika |
| 2007/0083245 A1* | 4/2007 | Lamensdorf et al. ........ 607/45 |
| 2007/0150034 A1 | 6/2007 | Rooney et al. |
| 2007/0179543 A1 | 8/2007 | Ben-David |
| 2007/0203527 A1 | 8/2007 | Ben-David |
| 2007/0255320 A1 | 11/2007 | Inman et al. |
| 2008/0004673 A1 | 1/2008 | Rossing et al. |
| 2008/0065158 A1 | 3/2008 | Ben-Ezra |
| 2008/0065184 A1 | 3/2008 | Hoffer et al. |
| 2008/0086180 A1 | 4/2008 | Ben-Ezra |
| 2008/0091245 A1 | 4/2008 | Ben-Ezra |
| 2008/0125819 A1 | 5/2008 | Ben-David |
| 2008/0125825 A1 | 5/2008 | Ben-Ezra |
| 2008/0125827 A1 | 5/2008 | Ben-David |
| 2008/0132983 A1 | 6/2008 | Cohen |
| 2008/0140141 A1 | 6/2008 | Ben-David |
| 2008/0172116 A1 | 7/2008 | Mrva et al. |
| 2008/0228238 A1 | 9/2008 | Libbus |
| 2008/0234780 A1 | 9/2008 | Smith |
| 2008/0275514 A1 | 11/2008 | Ben-David |
| 2009/0005845 A1 | 1/2009 | Ben David |
| 2009/0259315 A1 | 10/2009 | Banik |
| 2009/0275996 A1 | 11/2009 | Burnes et al. |
| 2010/0010603 A1 | 1/2010 | Ben-David |
| 2010/0042186 A1 | 2/2010 | Ben-David |
| 2010/0047376 A1 | 2/2010 | Imbeau et al. |
| 2010/0241195 A1 | 9/2010 | Meadows et al. |
| 2010/0241207 A1 | 9/2010 | Bluger |
| 2010/0312320 A1 | 12/2010 | Faltys et al. |
| 2011/0160827 A1 | 6/2011 | Bonde et al. |
| 2011/0196445 A1 | 8/2011 | Bolea et al. |
| 2011/0202106 A1 | 8/2011 | Bolea et al. |
| 2012/0095540 A1 | 4/2012 | Wahlstrand et al. |
| 2012/0130463 A1 | 5/2012 | Ben-David |
| 2012/0197371 A1 | 8/2012 | Neisz et al. |

FOREIGN PATENT DOCUMENTS

| | | |
|---|---|---|
| EP | 1785160 | 5/2007 |
| EP | 1897586 | 12/2008 |
| WO | 96/41655 | 12/1996 |
| WO | 01/10375 | 2/2001 |
| WO | 01/10432 | 2/2001 |
| WO | 01/26729 | 4/2001 |
| WO | 01/89526 | 11/2001 |
| WO | 02/085446 | 10/2002 |
| WO | 02/085448 | 10/2002 |
| WO | 02/087683 | 11/2002 |
| WO | 03/018113 | 3/2003 |
| WO | 03/094693 | 11/2003 |

(56) References Cited

FOREIGN PATENT DOCUMENTS

| | | |
|---|---|---|
| WO | 03/099373 | 12/2003 |
| WO | 03/099377 | 12/2003 |
| WO | 2004/028624 | 4/2004 |
| WO | 2004/047914 | 6/2004 |
| WO | 2004/052444 | 6/2004 |
| WO | 2004/103455 | 12/2004 |
| WO | 2004/110549 | 12/2004 |
| WO | 2004/110550 | 12/2004 |
| WO | 2006/057734 | 6/2006 |
| WO | 2006/102370 | 9/2006 |
| WO | 2006/126201 | 11/2006 |
| WO | 2007/113775 | 10/2007 |

OTHER PUBLICATIONS

Y. Zhang, et al., "Optimal Ventricular Rate Slowing During Atrial Fibrillation by Feedback AV Nodal-Selective Vagal Stimulation", Am J Physiol Heart Circ Physiol 282:H1102-H1110, 2002.

Billette J et al., "Roles of the AV junction in determining the ventricular response to atrial fibrillation," Can J Physiol Pharamacol 53(4)575-85 (1975).

Borovikova LV et al., "Vagus nerve stimulation attenuates the systemic inflammatory response to endotoxin," Nature 405(6785):458-62 (2000).

Gregory S. Friedrichs, "Experimental models of atrial fibrillation/flutter", Journal of Pharmacological and Toxoligical Methods 43 (2000), 117-123.

Kamath et al., "Effect of vagal nerve electrostimulation on the power spectrum of heart rate variability in man," Pacing Clin Electrophysiol 15:235-43 (1992).

De Ferrari GM, "Vagal reflexes and survival during acute myocardial ischemia in conscious dogs with healed myocardial infarction," Am J Physiol 261(1 Pt 2):H63-9 (1991).

Feliciano L et al., "Vagal nerve stimulation during muscarinic and beta-adrenergic blockade causes significant coronary artery dilation," Cardiovasc Res 40(1):45-55 (1998).

Pagé PL et al., "Regional distribution of atrial electrical changes induced by stimulation of extracardiac and intracardiac neural elements," J Thorac Cardiovasc Surg. 109(2):377-88 (1995).

Furukawa Y et al., "Differential blocking effects of atropine and gallamine on negative chronotropic and dromotropic responses to vagus stimulation in anesthetized dogs," J Pharmacol Exp Ther. 251(3):797-802 (1989).

N.J.M Rijkhoff, et al., "Selective Stimulation of Small Diameter Nerve Fibers in a Mixed Bundle", Proceedings of the Annual Project Meeting Sensations/Neuros and Mid Term Review Meeting Neuros, Apr. 21-23, 1999.

U.S. Appl. No. 60/263,834, filed Jan. 25, 2001.
U.S. Appl. No. 60/383,157, filed May 23, 2002.
U.S. Appl. No. 60/668,275, filed Apr. 4, 2005.
U.S. Appl. No. 60/478,576, filed Jun. 13, 2003.

Randall WC ed., *Neural Regulation of the Heart*, Oxford University Press (1977), particularly pp. 100-106.

Armour JA et al. eds., *Neurocardiology*, Oxford University Press (1994).

Jones, J et al., "Activity of C Fibers cardiac vagal efferents in anaesthetized cats and rats", Journal of Physiology 507(3):869-880. 1998.

Martin PJ et al., "Phasic effects of repetitive vagal stimulation on atrial contraction," Circ. Res. 52(6):657-63 (1983).

Wallick DW et al., "Selective AV nodal vagal stimulation improves hemodynamics during acute atrial fibrillation in dogs," Am J Physiol Heart Circ Physiol 281: H1490-H1497 (2001).

Fuster V and Ryden Le et al., "ACC/AHA/ESC Practice Guidelines—Executive Summary," J Am Coll Cardiol 38(4):1231-65 (2001).

Waninger MS et al., "Electrophysiological control of ventricular rate during atrial fibrillation," PACE 23:1239-1244 (2000).

Wijffels MC et al., "Electrical remodeling due to atrial fibrillation in chronically instrumented conscious goats: roles of neurohumoral changes, ischemia, atrial stretch, and high rate of electrical activation," Circulation 96(10):3710-20 (1997).

Wijffels MC et al., "Atrial fibrillation begets atrial fibrillation," Circulation 92:1954-1968 (1995).

Goldberger AL et al., "Vagally-mediated atrial fibrillation in dogs: conversion with bretylium tosylate," Int J Cardiol 13(1):47-55 (1986).

Takei M et al., "Vagal stimulation prior to atrial rapid pacing protects the atrium from electrical remodeling in anesthetized dogs," Jpn Circ J 65(12):1077-81 (2001).

Hayashi H et al., "Different effects of class Ic and III antiarrhythmic drugs on vagotonic atrial fibrillation in the canine heart," Journal of Cardiovascular Pharmacology 31:101-107 (1998).

Morady F et al., "Effects of resting vagal tone on accessory atrioventricular connections," Circulation 81(1):86-90 (1990).

Lew SJ et al., "Stroke prevention in elderly patients with atrial fibrillation," Singapore Med J 43(4):198-201 (2002).

Higgins CB, "Parasympathetic control of the heart," Pharmacol. Rev. 25:120-155 (1973).

Bibevski S et al., "Ganglionic Mechanisms Contribute to Diminished Vagal Control in Heart Failure," Circulation 99:2958-2963 (1999).

Bilgutay et al., in "Vagal tuning: a new concept in the treatment of supraventricular arrhythmias, angina pectoris, and heart failure," J. Thoracic Cardiovas. Surg. 56(1):71-82, Jul. 1968.

Li D et al., "Promotion of Atrial Fibrillation by Heart Failure in Dogs: Atrial Remodeling of a Different Sort," Circulation 100(1):87-95 (1999).

Deurloo KE et al., "Transverse tripolar stimulation of peripheral nerve: a modelling study of spatial selectivity," Med Biol Eng Comput, 36(1):66-74 (1998).

Goodall EV et al., "Position-selective activation of peripheral nerve fibers with a cuff electrode," IEEE Trans Biomed Eng, 43(8):851-6 (1996).

Jidéus Lena, "Atrial fibrillation after coronary artery bypass surgery: A study of causes and risk factors," Acta Universitatis Upsaliensis, Uppsala, Sweden (2001).

Manfredi M, "Differential block of conduction of larger fibers in peripheral nerve by direct current," Arch. Ital. Biol., 108:52-71 (1970).

Masato Tsuboi et al., "Inotropic, chronotropic, and dromotropic effects mediated via parasympathetic ganglia in the dog heart," Am J Physiol Heart Circ Physiol 279: H1201-H1207 (2000).

Mushahwar VK et al., "Muscle recruitment through electrical stimulation of the lumbo-sacral spinal cord," IEEE Trans Rehabil Eng, 8(1):22-9 (2000).

Carlson MD et al., "Selective stimulation of parasympathetic nerve fibers to the human sinoatrial node," Circulation 85:1311-1317 (1992).

Bluemel KM, "Parasympathetic postganglionic pathways to the sinoatrial node," J Physiol 259(5 Pt 2):H1504-10 (1990).

Grill WM et al., "Inversion of the current-distance relationship by transient depolarization," IEEE Trans Biomed Eng, 44(1):1-9 (1997).

Kwan H et al., "Cardiovascular adverse drug reactions during initiation of antiarrhythmic therapy for atrial fibrillation," Can J Hosp Pharm 54:10-14 (2001).

Naples GG et al., "A spiral nerve cuff electrode for peripheral nerve stimulation," by IEEE Transactions on Biomedical Engineering, 35(11) (1988).

Garrigue S et al., "Post-ganglionic vagal stimulation of the atrioventricular node reduces ventricular rate during atrial fibrillation," PACE 21(4), 878 (Part II) (1998).

Pagé PL et al., "Regional distribution of atrial electrical changes induced by stimulation of extracardiac and intracardiac neural elements," J Thorac Cardiovasc Surg 109(2):377-88 (1995).

Rijkhoff NJ et al., "Orderly recruitment of motoneurons in an acute rabbit model," Ann. Conf. of the IEEE Eng., Medicine and Biology Soc., 20(5):2564 (1998).

Rijkhoff NJ et al., "Acute animal studies on the use of anodal block to reduce urethral resistance in sacral root stimulation," IEEE Transactions on Rehabilitation Engineering, 2(2):92 (1994).

Mazgalev TN, "AV Nodal Physiology," Heart Rhythm Society (www.hrsonline.org).

(56) References Cited

OTHER PUBLICATIONS

An International Search Report and a Written Opinion both dated Jun. 1, 2005 which issued during the prosecution of Applicant's PCT/IL2004/000440.
An International Search Report and a Written Opinion both dated Mar. 31, 2005 which issued during the prosecution of Applicant's PCT/IL2004/000496.
An International Preliminary Report on Patentability dated Mar. 13, 2005, which issued during the prosecution of Applicant's PCT/IL2004/000496.
An International Search Report and a Written Opinion both dated Mar. 31, 2005 which issued during the prosecution of Applicant's PCT/IL2004/000495.
Chen Shih-Ann et al., "Intracardiac stimulation of human parasympathetic nerve fibers induces negative dromotropic effects: implication with the lesions of radiofrequency catheter ablation," J Cardiovasc Electrophysiol 9(3):245-52 (1998).
An International Preliminary Report on Patentability and a Written Opinion both dated Nov. 25, 2005, which issued during the prosecution of Applicant's PCT/IL2004/000440.
Rijkhoff NJ et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999).
Cooper TB et al., "Neural effects on sinus rate and atrial ventricular conduction produced by electrical stimulation from a transvenous electrode catheter in the canine right pulmonary artery" Circ Res vol. 46(1):48-57 (1980).
Veraart C et al., "Selective control of muscle activation with a multipolar nerve cuff electrode," IEEE Trans Biomed Eng, 40(7):640-53 (1993).
Tarver WB et al., "Clinical experience with a helical bipolar stimulating lead," Pace, vol. 15, October, Part II (1992).
Ungar IJ et al., "Generation of unidirectionally propagating action potentials using a monopolar electrode cuff," Annals of Biomedical Engineering, 14:437-450 (1986).
Van den Honert C et al., "Generation of unidirectionally propagated action potentials in a peripheral nerve by brief stimuli," Science, 206:1311-1312 (1979).
Van den Honert C et al., "A technique for collision block of peripheral nerve: Frequency dependence," MP-12, IEEE Trans. Biomed. Eng. 28:379-382 (1981).
Sweeney JD et al., "An asymmetric two electrode cuff for generation of unidirectionally propagated action potentials," IEEE Transactions on Biomedical Engineering, vol. BME-33(6) (1986).
Sweeney JD et al., "A nerve cuff technique for selective excitation of peripheral nerve trunk regions," IEEE Transactions on Biomedical Engineering, 37(7) (1990).
Levy MN, Blattberg B., "Effect of vagal stimulation on the overflow of norepinephrine into the coronary sinus during sympathetic nerve stimulation in the dog," Circ Res Feb. 1976; 38(2):81-4.
Stramba-Badiale M et al., "Sympathetic-Parasympathetic Interaction and Accentuated Antagonism in Conscious Dogs," American Journal of Physiology 260 (2Pt 2):H335-340 (1991).
Vanoli E et al., "Vagal stimulation and prevention of sudden death in conscious dogs with a healed myocardial infarction," Circ Res 68(5):1471-81 (1991).
Wang H et al., "Nicotinic acetylcholine receptor alpha-7 subunit is an essential regulator of inflammation," Nature 421:384-388 (2003).
Baratta R et al., "Orderly stimulation of skeletal muscle motor units with tripolar nerve cuff electrode," IEEE Transactions on Biomedical Engineering, 36(8):836-43 (1989).
Fitzpatrick et al., in "A nerve cuff design for the selective activation and blocking of myelinated nerve fibers," Ann. Conf. of the IEEE Eng. in Medicine and Biology Soc, 13(2), 906 (1991).
Levy MN et al. ed., Vagal Control of the Heart: Experimental Basis and Clinical Implications (The Bakken Research Center Series vol. 7), Futura Publishing Company, Inc., Armonk, NY (1993).

Morillo CA et al., "Chronic rapid atrial pacing. Structural, functional, and electrophysiological characteristics of a new model of sustained atrial fibrillation," Circulation 91:1588-1595 (1995).
Hirose M et al., "Pituitary Adenylate Cyclase-Activating Polypeptide-27 Causes a Biphasic Chronotropic Effect and Atrial Fibrillation in Autonomically Decentralized, Anesthetized Dogs," J Pharmacol Exp Ther 283(2):478-87 (1997).
Chiou, C.W., et al. "Efferent vagal innervations of the canine atria and sinus and atrioventricular nodes", Circulation, 1997 vol. 95 p. 2573.
P. Schauerte, et al. "Catheter Stimulation of cariac parasympathetic nerves in humans", pp. 2430-2435, 2001.
Schaldach M "New concepts in electrotherapy of the heart", Electrotherapy of the heart, Springer Verlag Hiedelberg, pp. 210-214 (1992).
Jones, JFX et al., "Heart rate responses to selective stimulation of cardiac vagal C fibres in anaesthetized cats, rats and rabbits," J Physiol 489 (Pt 1):203-14 (1995).
Perez MG et al. Effect of Stimulating non-myelinated vagal axon on atrioventricular conduction and left ventricular function in anaesthetized rabbits, Auton Neurosco 86 (2001).
Wallick DW et al., Effects of ouabain and vagal stimulation on heart rate in the dog, Cardiovasc. Res., 18(2):75-9 (1984).
Wallick DW et al., "Effects of repetitive bursts of vagal activity on atrioventricular junctional rate in dogs," Am J Physiol 237(3):H275-81 (1979).
Hunt R, "Experiments on the relations of the inhibitory to the accelerator nerves of the heart," J. Exptl. Med. 2:151-179 (1897).
Sabbah HN et al., "A canine model of chronic heart failure produced by multiple sequential coronary microembolizations," Am J Physiol 260:H1379-1384 (1991).
Tetsu Iwao et al., Effect of Constant and Intermittent Vagal Stimulation on the Heart Rate and Heart Rate Variability in Rabbits. Japanese Journal of Physiology, 50, 33-39, 2000.
Mitsuhiro Kudo et al. Implantation of bone marrow stem cell reduce the infraction and fibrosis in ischemic mouse heart., Journal of Molecular and Cellular Cardiology 35 (2003) 1113-1119.
Takayama et al., A Possible Involvement of Parasympathetic Neuropathy on Insulin Resistance in Patient with Type 2 Diabetes. Diabetes Care, vol. 24 No. 5 May 2001, 968-969.
Thomas R. Bernik, Pharmacological Stimulation of the Cholinergic Antiinflammatory Pathway. The Rockefeller University Press, vol. 195, No. 6 Mar. 18, 2002, 781-788.
An Office Action dated Apr. 7, 2009, which issued during the prosecution of European Patent Application No. 07253557.
An Office Action dated Oct. 6, 2010, which issued during the prosecution of European Patent Application No. 02716294.
An Office Action dated Apr. 3, 2009, which issued during the prosecution of European Patent Application No. 02716294.
An Office Action dated Jul. 30, 2012 which issued during the prosecution of U.S. Appl. No. 11/978,440.
An Office Action dated Jun. 24, 2009, which issued during the prosecution of U.S. Appl. No. 11/978,379.
An Office Action dated Jun. 23, 2010, which issued during the prosecution of U.S. Appl. No. 11/978,379.
An Office Action dated Jul. 27, 2011, which issued during the prosecution of U.S. Appl. No. 11/975,654.
An Office Action dated May 12, 2010, which issued during the prosecution of U.S. Appl. No. 11/975,241.
An Office Action dated Mar. 30, 2010, which issued during the prosecution of U.S. Appl. No. 11/517,888.
An Office Action dated Sep. 4 2009, which issued during the prosecution of U.S. Appl. No. 11/234,877.
An Office Action dated Feb. 24, 2010, which issued during the prosecution of U.S. Appl. No. 11/234,877.
An Office Action dated Feb. 19, 2009, which issued during the prosecution of U.S. Appl. No. 11/234,877.
An Office Action dated May 31, 2012, which issued during the prosecution of U.S. Appl. No. 11/070,842.
An Office Action dated Jun. 23, 2011, which issued during the prosecution of U.S. Appl. No. 11/070,842.
An Office Action dated Jul. 21, 2009, which issued during the prosecution of U.S. Appl. No. 11/070,842.
An Office Action dated Jul. 12, 2010, which issued during the prosecution of U.S. Appl. No. 11/070,842.

(56) References Cited

OTHER PUBLICATIONS

An Office Action dated Oct. 9, 2008, which issued during the prosecution of U.S. Appl. No. 11/644,446.
An Office Action dated Nov. 9, 2009, which issued during the prosecution of U.S. Appl. No. 11/644,446.
An Office Action dated Jun. 29, 2010, which issued during the prosecution of U.S. Appl. No. 11/644,446.
An Office Action dated Jun. 15, 2009, which issued during the prosecution of U.S. Appl. No. 11/644,446.
An Office Action dated Feb. 18, 2009, which issued during the prosecution of U.S. Appl. No. 11/062,324.
An Office Action dated Aug. 11, 2008, which issued during the prosecution of U.S. Appl. No. 11/062,324.
An Office Action dated Mar. 26, 2008, which issued during the prosecution of U.S. Appl. No. 10/866,601.
An Office Action dated Oct. 29, 2007, which issued during the prosecution of U.S. Appl. No. 10/866,601.
An Office Action dated Nov. 24, 2006, which issued during the prosecution of U.S. Appl. No. 10/866,601.
An Office Action dated Feb. 24, 2010, which issued during the prosecution of U.S. Appl. No. 10/866,601.
An Office Action dated Oct. 30, 2007, which issued during the prosecution of U.S. Appl. No. 10/722,589.
An Office Action dated Mar. 17, 2010, which issued during the prosecution of U.S. Appl. No. 10/722,589.
An Office Action dated Mar. 7, 2006, which issued during the prosecution of U.S. Appl. No. 10/722,589.
An Office Action dated Nov. 28, 2007, which issued during the prosecution of U.S. Appl. No. 10/719,659.
An Office Action dated Apr. 28, 2009, which issued during the prosecution of U.S. Appl. No. 10/719,659.
An Office Action dated Jul. 9, 2008, which issued during the prosecution of U.S. Appl. No. 10/560,564.
An Office Action dated Feb. 11, 2009, which issued during the prosecution of U.S. Appl. No. 10/560,654.
An Office Action dated Oct. 16, 2009, which issued during the prosecution of U.S. Appl. No. 10/488,334.
An Office Action dated Apr. 5, 2007, which issued during the prosecution of U.S. Appl. No. 10/488,334.
An Office Action dated Jul. 31, 2007, which issued during the prosecution of U.S. Appl. No. 10/461,696.
An Office Action dated Mar. 15, 2007, which issued during the prosecution of U.S. Appl. No. 10/461,696.
An Office Action dated Jun. 3, 2005, which issued during the prosecution of U.S. Appl. No. 10/461,696.
An Office Action dated Oct. 23, 2006, which issued during the prosecution of U.S. Appl. No. 10/205,475.
An Office Action dated Nov. 2007, which issued during the prosecution of U.S. Appl. No. 10/205,475.
An Office Action dated Jan. 11, 2006, which issued during the prosecution of U.S. Appl. No. 10/205,475.
An Office Action dated Feb. 26, 2007, which issued during the prosecution of U.S. Appl. No. 10/205,475.
An Office Action dated Jan. 15, 2004, which issued during the prosecution of U.S. Appl. No. 10/205,474.
An Office Action dated Jan. 5, 2011, which issued during the prosecution of U.S. Appl. No. 11/978,379.
An Office Action dated Jul. 28, 2010, which issued during the prosecution of U.S. Appl. No. 11/975,241.
An Office Action dated Aug. 25, 2009, which issued during the prosecution of U.S. Appl. No. 11/975,241.
An Office Action dated Aug. 21, 2009, which issued during the prosecution of U.S. Appl. No. 11/975,169.
An Office Action dated Nov. 19, 2007, which issued during the prosecution of U.S. Appl. No. 10/560,654.
A Notice of Allowance dated Apr. 23, 2012, which issued during the prosecution of U.S. Appl. No. 11/975,654.
A Notice of Allowance dated Dec. 14, 2009, which issued during the prosecution of U.S. Appl. No. 11/975,169.
A Notice of Allowance dated Oct. 28, 2010, which issued during the prosecution of U.S. Appl. No. 11/517,888.
A Notice of Allowance dated Sep. 27, 2010, which issued during the prosecution of U.S. Appl. No. 11/234,877.
A Notice of Allowance dated Nov. 3, 2009, which issued during the prosecution of U.S. Appl. No. 11/062,324.
A Notice of Allowance dated Nov. 12, 2010, which issued during the prosecution of U.S. Appl. No. 10/722,589.
A Notice of Allowance dated Apr. 5, 2010, which issued during the prosecution of U.S. Appl. No. 10/719,659.
A Notice of Allowance dated Dec. 6, 2010, which issued during the prosecution of U.S. Appl. No. 10/560,654.
A Notice of Allowance dated Mar. 22, 2010, which issued during the prosecution of U.S. Appl. No. 10/488,334.
A Notice of Allowance dated Oct. 17, 2007, which issued during the prosecution of U.S. Appl. No. 10/461,696.
A Notice of Allowance dated Jun. 17, 2004, which issued during the prosecution of U.S. Appl. No. 10/205,474.
A Notice of Allowance dated Jun. 21, 2011, which issued during the prosecution of U.S. Appl. No. 11/978,379.
A European Search Report dated Jan. 28, 2008 which issued during the prosecution of European Patent Application No. 07253557.
An International Preliminary Report on Patentability dated Mar. 25, 2004 and International Search Report dated Dec. 23, 2002, which issued during the prosecution of Applicant's PCT/IL2002/000068.
An Office Action dated Nov. 21, 2012, which issued during the prosecution of U.S. Appl. No. 12/952,058.
An Office Action dated Jan. 22, 2013, which issued during the prosecution of U.S. Appl. No. 13/022,279.
An Office Action dated Mar. 29, 2013, which issued during the prosecution of U.S. Appl. No. 11/340,156.
Skale et al. "Inhibition of Premature Ventricular Extrastimuli by Subthreshold Conditioning Stimuli", JACC vol. 6 No. 1 Jul. 1985: 133-40.

* cited by examiner

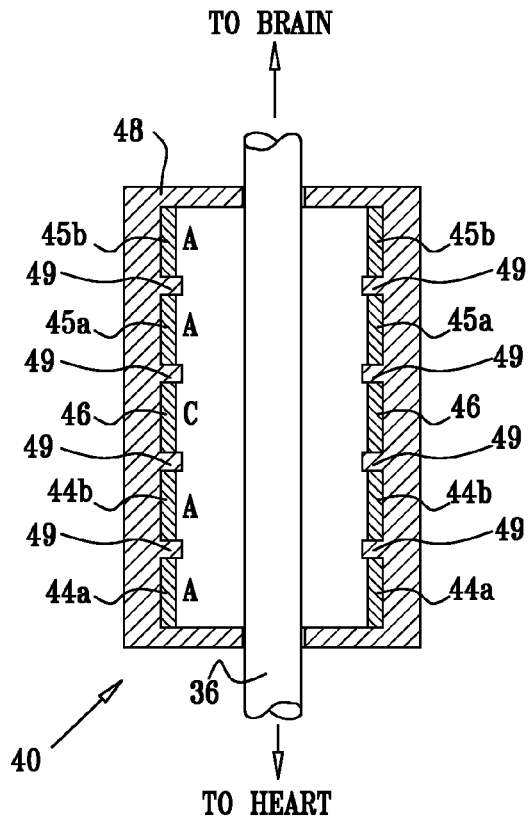
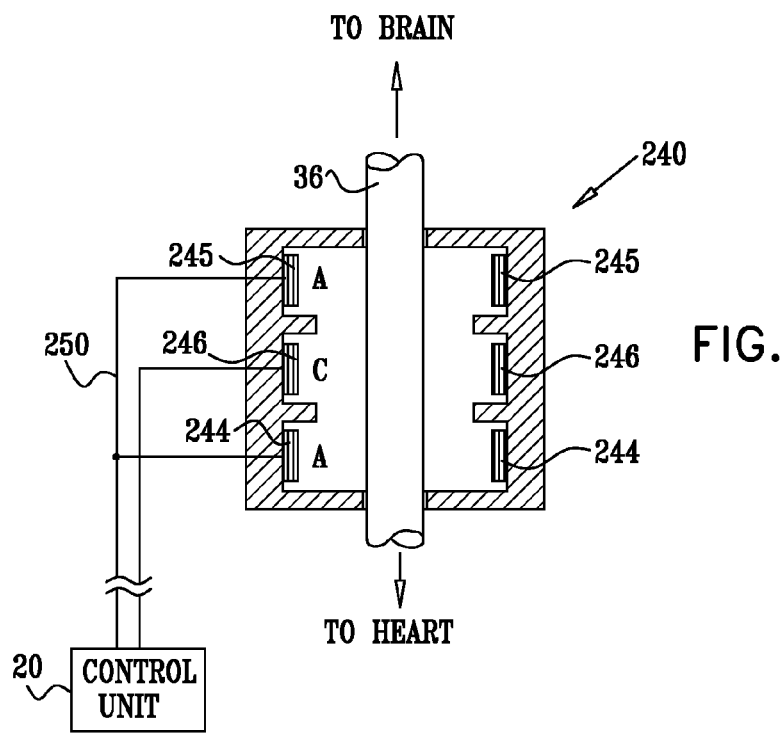

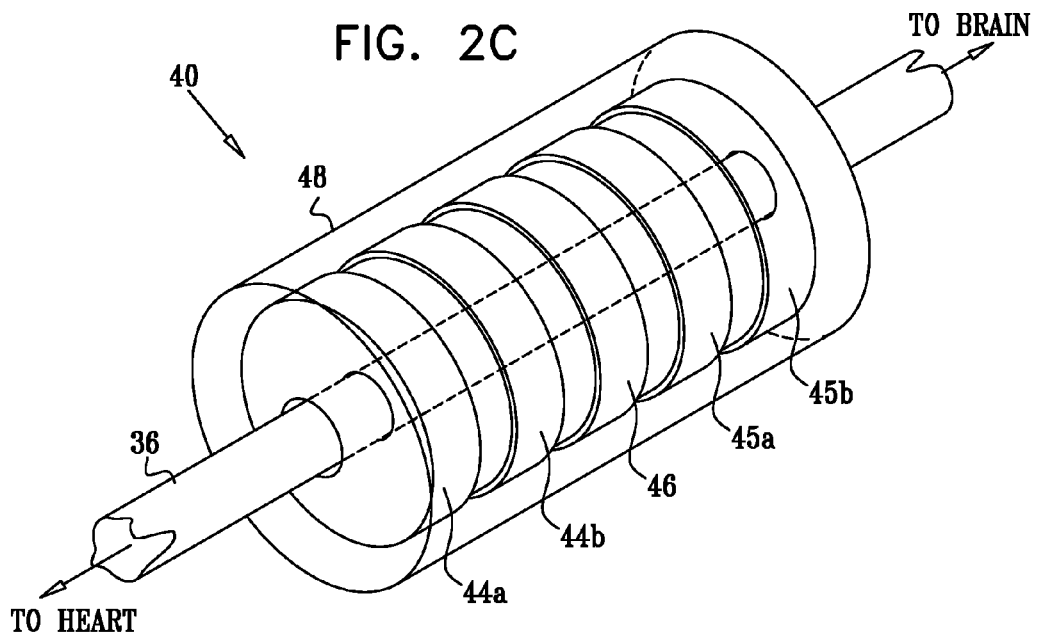
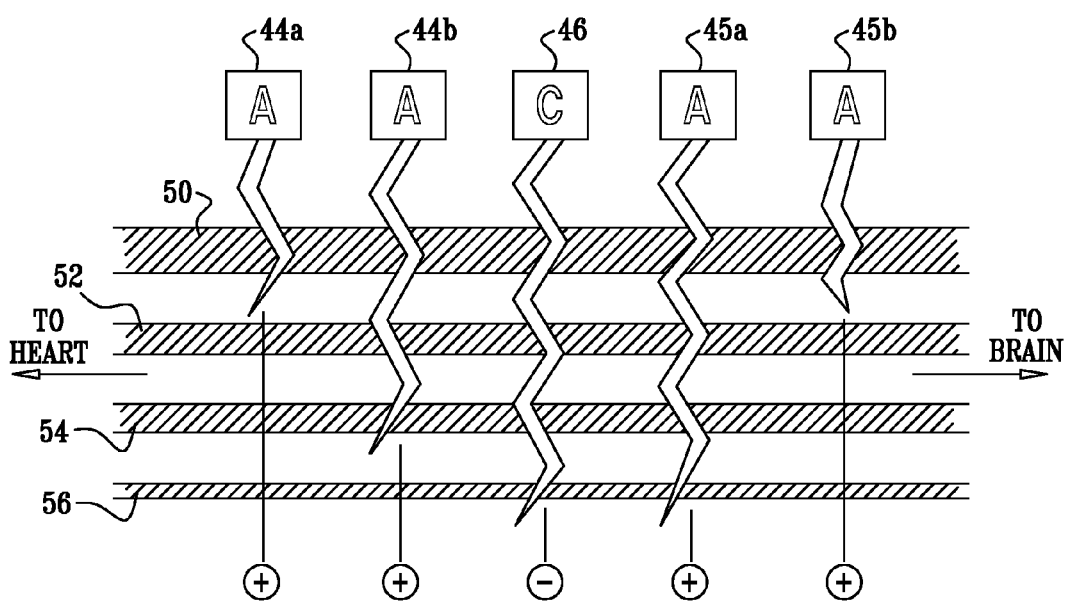

TECHNIQUES FOR REDUCING PAIN ASSOCIATED WITH NERVE STIMULATION

CROSS-REFERENCES TO RELATED APPLICATIONS

The present application is a divisional of U.S. application Ser. No. 11/517,888, filed Sep. 7, 2006, now U.S. Pat. No. 7,904,176, which is related to: (a) U.S. application Ser. No. 11/064,446, filed Feb. 22, 2005, now U.S. Pat. No. 7,974,693, and (b) U.S. application Ser. No. 11/062,324, filed Feb. 18, 2005, now U.S. Pat. No. 7,634,317. All of the above-mentioned applications are assigned to the assignee of the present application and are incorporated herein by reference.

FIELD OF THE INVENTION

The present invention relates generally to treating subjects by application of electrical signals to a selected nerve or nerve bundle, and specifically to methods and apparatus for reducing pain associated with nerve stimulation.

BACKGROUND OF THE INVENTION

The use of nerve stimulation for treating and controlling a variety of medical, psychiatric, and neurological disorders has seen significant growth over the last several decades. In particular, stimulation of the vagus nerve (the tenth cranial nerve, and part of the parasympathetic nervous system) has been the subject of considerable research. The vagus nerve is composed of somatic and visceral afferents (inward conducting nerve fibers, which convey impulses toward the brain) and efferents (outward conducting nerve fibers, which convey impulses to an effector to regulate activity such as muscle contraction or glandular secretion).

The rate of the heart is restrained in part by parasympathetic activity from the right and left vagus nerves. Low vagal nerve activity is considered to be related to various arrhythmias, including tachycardia, ventricular accelerated rhythm, and rapid atrial fibrillation. By artificially stimulating the vagus nerves, it is possible to slow the heart, allowing the heart to more completely relax and the ventricles to experience increased filling. With larger diastolic volumes, the heart may beat more efficiently because it may expend less energy to overcome the myocardial viscosity and elastic forces of the heart with each beat.

Stimulation of the vagus nerve has been proposed as a method for treating various heart conditions, including heart failure and atrial fibrillation. Heart failure is a cardiac condition characterized by a deficiency in the ability of the heart to pump blood throughout the body and/or to prevent blood from backing up in the lungs. Customary treatment of heart failure includes medication and lifestyle changes. It is often desirable to lower the heart rates of subjects suffering from faster than normal heart rates. The effectiveness of beta blockers in treating heart disease is attributed in part to their heart-rate-lowering effect.

Bilgutay et al., in "Vagal tuning: a new concept in the treatment of supraventricular arrhythmias, angina pectoris, and heart failure," J. Thoracic Cardiovas. Surg. 56(1):71-82, July, 1968, which is incorporated herein by reference, studied the use of a permanently-implanted device with electrodes to stimulate the right vagus nerve for treatment of supraventricular arrhythmias, angina pectoris, and heart failure. Experiments were conducted to determine amplitudes, frequencies, wave shapes and pulse lengths of the stimulating current to achieve slowing of the heart rate. The authors additionally studied an external device, triggered by the R-wave of the electrocardiogram (ECG) of the subject to provide stimulation only upon an achievement of a certain heart rate. They found that when a pulsatile current with a frequency of ten pulses per second and 0.2 milliseconds pulse duration was applied to the vagus nerve, the heart rate could be decreased to half the resting rate while still preserving sinus rhythm. Low amplitude vagal stimulation was employed to control induced tachycardias and ectopic beats. The authors further studied the use of the implanted device in conjunction with the administration of Isuprel, a sympathomimetic drug. They found that Isuprel retained its inotropic effect of increasing contractility, while its chronotropic effect was controlled by the vagal stimulation: "An increased end diastolic volume brought about by slowing of the heart rate by vagal tuning, coupled with increased contractility of the heart induced by the inotropic effect of Isuprel, appeared to increase the efficiency of cardiac performance" (p. 79).

US Patent Application Publications 2005/0197675 and 2005/0267542 to Ben-David, which are assigned to the assignee of the present application and is incorporated herein by reference, describe apparatus including an electrode device, adapted to be coupled to a site of a subject; and a control unit, adapted to drive the electrode device to apply a current to the site intermittently during alternating "on" and "off" periods, each of the "on" periods having an "on" duration equal to between 1 and 10 seconds, and each of the "off" periods having an "off" duration equal to at least 50% of the "on" duration. In some embodiments, the control unit is configured to gradually ramp the commencement and/or termination of stimulation. In order to achieve the gradual ramp, the control unit is typically configured to gradually modify one or more stimulation parameters, such as those described hereinabove, e.g., pulse amplitude, pulses per trigger (PPT), pulse frequency, pulse width, "on" time, and/or "off" time. As appropriate, one or more of these parameters are varied by less than 50% of a pre-termination value per heart beat, in order to achieve the gradual ramp. For example, stimulation at 5 PPT may be gradually terminated by reducing the PPT by 1 pulse per hour. Alternatively, one or more of the parameters are varied by less than 5% per heart beat, in order to achieve the gradual ramp.

U.S. Pat. No. 6,167,304 to Loos, which is incorporated herein by reference, describes techniques for manipulating the nervous system of a subject by applying to the skin a pulsing external electric field which, although too weak to cause classical nerve stimulation, modulates the normal spontaneous spiking patterns of certain kinds of afferent nerves. For certain pulse frequencies the electric field stimulation can excite in the nervous system resonances with observable physiological consequences. Pulse variability is introduced for the purpose of thwarting habituation of the nervous system to the repetitive stimulation, or to alleviate the need for precise tuning to a resonance frequency, or to control pathological oscillatory neural activities such as tremors or seizures. Pulse generators with stochastic and deterministic pulse variability are described, and the output of a generator of the latter type is characterized. Techniques for achieving pulse variability include ramping the pulse frequency in time, or switching the pulses on and off according to a certain schedule determined by dedicated digital circuitry or by a programmable microprocessor.

US Patent Application Publication 2005/0222644 to Killian et al., which is incorporated herein by reference, describes a method for stimulating nerve or tissue fibers and a prosthetic hearing device implementing same. The method comprises: generating a stimulation signal comprising a plurality of pulse bursts each comprising a plurality of pulses; and distributing said plurality of pulse bursts across one or more electrodes each operatively coupled to nerve or tissue fibers such that each of said plurality of pulse bursts delivers a charge to said nerve or tissue fibers to cause dispersed firing in said nerve or tissue fibers. In an embodiment, individual pulses of a pulse burst are non-repeatedly interleaved on three channels. Multiple pulses may be repeated on one channel.

U.S. Pat. No. 5,562,718 to Palermo, which is incorporated herein by reference, describes an electronic neuromuscular stimulation device that is operated by a control unit. The control unit includes at least two output channels to which are connected to a corresponding set of electrode output cables. Each cable has attached a positive electrode and a negative electrode that are attached to selected areas of a patient's anatomy. The control unit also includes controls, indicators, and circuitry that produce nerve stimulation pulses that are applied to the patient through the electrodes. The nerve stimulation pulses consist of individual pulses that are arranged into pulse trains and pulse train patterns. The pulse train patterns, whose selection depends on the type of ailment being treated, includes sequential patterns, delayed overlapping patterns, triple-phase overlapping patterns, reciprocal pulse trains, and delayed sequenced "sprint interval" patterns. The overlapping patterns are described as being particularly timed to take advantage of neurological enhancement. In an embodiment, the pulse trains operate at a pulse rate interval of between 10 and 20 milliseconds which corresponds to a frequency of between 50 Hz and 100 Hz respectively. If a ramp frequency is used, it is applied just prior to the application of a long pulse train. The ramp frequency varies between 18 and 50 Hz and progresses over a 0.5 to 2.0 second period.

U.S. Pat. No. 5,707,400 to Terry, Jr. et al., which is incorporated herein by reference, describes a method for treating patients suffering from refractory hypertension, which includes identifying a patient suffering from the disorder and applying a stimulating electrical signal to the patient's vagus nerve predetermined to modulate the electrical activity of the nerve and to alleviate the hypertension. The stimulating signal is a pulse waveform with programmable signal parameter values including pulse width, output current, frequency, on time and off time. Patient discomfort may be alleviated by a ramping up the pulses during the first two seconds of stimulation, rather than abrupt application at the programmed level.

U.S. Pat. No. 6,928,320 to King, which is incorporated herein by reference, describes techniques for producing a desired effect by therapeutically activating tissue at a first site within a patient's body, and reducing a corresponding undesired side effect by blocking activation of tissue or conduction of action potentials at a second site within the patient's body by applying high frequency stimulation and/or direct current pulses at or near the second site. Time-varying DC pulses may be used before or after a high frequency blocking signal. The high frequency stimulation may begin before and continue during the therapeutic activation. The high frequency stimulation may begin with a relatively low amplitude, and the amplitude may be gradually increased. The desired effect may be promotion of micturition or defecation and the undesired side effect may be sphincter contraction. The desired effect may be defibrillation of the patient's atria or defibrillation of the patient's ventricles, and the undesired side effect may be pain. In an embodiment, the amplitude of the pulse waveform is ramped up or gradually increased at the beginning of the waveform, and ramped down or gradually decreased at the end of the waveform, respectively. Such ramping may be used in order to minimize creation of any action potentials that may be caused by more abruptly starting and/or more abruptly stopping the high frequency blocking stimulation.

US Patent Application Publication 2006/0129205 to Boveja et al., which is incorporated herein by reference, describes techniques for providing rectangular and/or complex electrical pulses to cortical tissues of a patient for at least one of providing therapy or alleviating symptoms of neurological disorders including Parkinson's disease, or for providing improvement of functional recovery following stroke. The intracranial electrodes may be implanted epidurally, or subdurally on the pia mater of the cortical surface. In an embodiment, a microcontroller is configured to deliver a pulse train by "ramping up" of the pulse train. The purpose of the ramping-up is to avoid sudden changes in stimulation when the pulse train begins.

U.S. Pat. No. 6,895,280 to Meadows et al., which is incorporated herein by reference, describes a spinal cord stimulation (SCS) system that includes multiple electrodes, multiple, independently programmable, stimulation channels within an implantable pulse generator (IPG) which channels can provide concurrent, but unique stimulation fields, permitting virtual electrodes to be realized. If slow start/end is enabled, the stimulation intensity is ramped up gradually when the IPG is first turned ON. If slow start/end is enabled, the stimulation intensity may be ramped down gradually rather than abruptly turned off. In an embodiment, a pulse ramping control technique for providing a slow turn-on of the stimulation burst includes modulating pulse amplitude at the beginning of a stimulation burst, while maintaining the pulse width as wide as possible, e.g., as wide as the final pulse duration.

US Patent Application Publication 2006/0015153A1 to Gliner et al., which is incorporated herein by reference, describes techniques for enhancing or affecting neural stimulation efficiency and/or efficacy. In one embodiment, electromagnetic stimulation is applied to a patient's nervous system over a first time domain according to a first set of stimulation parameters, and over a second time domain according to a second set of stimulation parameters. The first and second time domains may be sequential, simultaneous, or nested. Stimulation parameters may vary in accordance with one or more types of duty cycle, amplitude, pulse repetition frequency, pulse width, spatiotemporal, and/or polarity variations. Stimulation may be applied at subthreshold, threshold, and/or suprathreshold levels in one or more periodic, aperiodic (e.g., chaotic), and/or pseudo-random manners. In some embodiments stimulation may comprise a burst pattern having an interburst frequency corresponding to an intrinsic brainwave frequency, and regular and/or varying intraburst stimulation parameters. In an embodiment, within a time interval under consideration (e.g., 250 milliseconds), an interpulse interval of 8 milliseconds may occur 5 times; an interpulse interval of 10 milliseconds may occur 8 times; an interpulse interval of 12 milliseconds may occur 6 times; an interpulse interval of 14 milliseconds may occur 2 times; and interpulse intervals of 16 milliseconds and 18 milliseconds may each occur once.

U.S. Pat. No. 5,330,507 to Schwartz, which is incorporated herein by reference, describes techniques for stimulating the right or left vagus nerve with continuous and/or phasic electrical pulses, the latter in a specific relationship with the R-wave of the patient's electrogram. The automatic detection of the need for vagal stimulation is responsive to increases in the heart rate greater than a predetermined threshold, the occurrence of frequent or complex ventricular arrhythmias, and/or a change in the ST segment elevation greater than a predetermined or programmed threshold.

US Patent Application Publication 2003/0040774 to Terry et al., which is incorporated herein by reference, describes a device for treating patients suffering from congestive heart failure that includes an implantable neurostimulator for stimulating the patient's vagus nerve at or above the cardiac branch with an electrical pulse waveform at a stimulating rate sufficient to maintain the patient's heart beat at a rate well below the patient's normal resting heart rate, thereby allowing rest and recovery of the heart muscle, to increase in coronary blood flow, and/or growth of coronary capillaries. A metabolic need sensor detects the patient's current physical state and concomitantly supplies a control signal to the neurostimulator to vary the stimulating rate. If the detection indicates a state of rest, the neurostimulator rate reduces the patient's heart rate below the patient's normal resting rate. If the detection indicates physical exertion, the neurostimulator rate increases the patient's heart rate above the normal resting rate.

U.S. Pat. No. 5,203,326 to Collins, which is incorporated herein by reference, describes an antiarrhythmia pacemaker which detects a cardiac abnormality and responds with electrical stimulation of the heart combined with vagus nerve stimulation. The pacemaker controls electrical stimulation of the heart in terms of timing, frequency, amplitude, duration and other operational parameters, to provide such pacing therapies as antitachycardia pacing, cardioversion, and defibrillation. The vagal stimulation frequency is progressively increased in one-minute intervals, and, for the pulse delivery rate selected, the heart rate is described as being slowed to a desired, stable level by increasing the pulse current.

The following patent and patent application publications, all of which are incorporated herein by reference, may be of interest:

U.S. Pat. No. 6,473,644 to Terry, Jr. et al.
US Patent Publication 2003/0045909 to Gross et al.
U.S. Pat. No. 5,188,104 to Wernicke et al.
U.S. Pat. Nos. 6,272,377 and 6,400,982 to Sweeney et al.
U.S. Pat. Nos. 5,411,531 and 5,507,784 to Hill et al.
U.S. Pat. No. 6,628,987 to Hill et al.
U.S. Pat. No. 6,449,507 to Hill et al.
U.S. Pat. No. 6,542,774 to Hill et al.
US Patent Application 2003/0216775 to Hill et al.
US Patent Application 2002/0035335 to Schauerte
U.S. Pat. Nos. 6,240,314 and 6,493,585 to Plicchi et al.
U.S. Pat. No. 6,381,499 to Taylor et al.
U.S. Pat. No. 6,564,096 to Mest The effect of vagal stimulation on heart rate and other aspects of heart function, including the relationship between the timing of vagal stimulation within the cardiac cycle and the induced effect on heart rate, has been studied in animals. For example, Zhang Y et al., in "Optimal ventricular rate slowing during atrial fibrillation by feedback AV nodal-selective vagal stimulation," Am J Physiol Heart Circ Physiol 282:H1102-H1110 (2002), describe the application of selective vagal stimulation by varying the nerve stimulation intensity, in order to achieve graded slowing of heart rate. This article is incorporated herein by reference.

The following articles and book, which are incorporated herein by reference, may be of interest:

Levy M N et al., in "Parasympathetic Control of the Heart," Nervous Control of Vascular Function, Randall W C ed., Oxford University Press (1984)

Levy M N et al. ed., Vagal Control of the Heart: Experimental Basis and Clinical Implications (The Bakken Research Center Series Volume 7), Futura Publishing Company, Inc., Armonk, N.Y. (1993)

Randall W C ed., Neural Regulation of the Heart, Oxford University Press (1977), particularly pages 100-106.

Armour J A et al. eds., Neurocardiology, Oxford University Press (1994)

Perez M G et al., "Effect of stimulating non-myelinated vagal axon on atrioventricular conduction and left ventricular function in anaesthetized rabbits," Auton Neurosco 86 (2001)

Jones, J F X et al., "Heart rate responses to selective stimulation of cardiac vagal C fibres in anaesthetized cats, rats and rabbits," J Physiol 489 (Pt 1):203-14 (1995)

Wallick D W et al., "Effects of ouabain and vagal stimulation on heart rate in the dog," Cardiovasc. Res., 18(2):75-9 (1984)

Martin P J et al., "Phasic effects of repetitive vagal stimulation on atrial contraction," Circ. Res. 52(6):657-63 (1983)

Wallick D W et al., "Effects of repetitive bursts of vagal activity on atrioventricular junctional rate in dogs," Am J Physiol 237(3):H275-81 (1979)

Wallick D W et al., "Selective AV nodal vagal stimulation improves hemodynamics during acute atrial fibrillation in dogs," Am J Physiol Heart Circ Physiol 281: H1490-H1497 (2001)

Fuster V and Ryden L E et al., "ACC/AHA/ESC Practice Guidelines—Executive Summary," J Am Coll Cardiol 38(4):1231-65 (2001)

Fuster V and Ryden L E et al., "ACC/AHA/ESC Practice Guidelines—Full Text," J Am Coll Cardiol 38(4):1266i-12661xx (2001)

Morady F et al., "Effects of resting vagal tone on accessory atrioventricular connections," Circulation 81(1):86-90 (1990)

Waninger M S et al., "Electrophysiological control of ventricular rate during atrial fibrillation," PACE 23:1239-1244 (2000)

Wijffels M C et al., "Electrical remodeling due to atrial fibrillation in chronically instrumented conscious goats: roles of neurohumoral changes, ischemia, atrial stretch, and high rate of electrical activation," Circulation 96(10):3710-20 (1997)

Wijffels M C et al., "Atrial fibrillation begets atrial fibrillation," Circulation 92:1954-1968 (1995)

Goldberger A L et al., "Vagally-mediated atrial fibrillation in dogs: conversion with bretylium tosylate," Int J Cardiol 13(1):47-55 (1986)

Takei M et al., "Vagal stimulation prior to atrial rapid pacing protects the atrium from electrical remodeling in anesthetized dogs," Jpn Circ J 65(12):1077-81 (2001)

Friedrichs G S, "Experimental models of atrial fibrillation/flutter," J Pharmacological and Toxicological Methods 43:117-123 (2000)

Hayashi H et al., "Different effects of class Ic and III antiarrhythmic drugs on vagotonic atrial fibrillation in the canine heart," Journal of Cardiovascular Pharmacology 31:101-107 (1998)

Morillo C A et al., "Chronic rapid atrial pacing. Structural, functional, and electrophysiological characteristics of a new model of sustained atrial fibrillation," Circulation 91:1588-1595 (1995)

Lew S J et al., "Stroke prevention in elderly patients with atrial fibrillation," Singapore Med J 43(4):198-201 (2002)

Higgins C B, "Parasympathetic control of the heart," Pharmacol. Rev. 25:120-155 (1973)

Hunt R, "Experiments on the relations of the inhibitory to the accelerator nerves of the heart," J. Exptl. Med. 2:151-179 (1897)

Billette J et al., "Roles of the AV junction in determining the ventricular response to atrial fibrillation," Can J Physiol Pharamacol 53(4)575-85 (1975)

Stramba-Badiale M et al., "Sympathetic-Parasympathetic Interaction and Accentuated Antagonism in Conscious Dogs," American Journal of Physiology 260 (2Pt 2):H335-340 (1991)

Garrigue S et al., "Post-ganglionic vagal stimulation of the atrioventricular node reduces ventricular rate during atrial fibrillation," PACE 21(4), 878 (Part II) (1998)

Kwan H et al., "Cardiovascular adverse drug reactions during initiation of antiarrhythmic therapy for atrial fibrillation," Can J Hosp Pharm 54:10-14 (2001)

Jidéus L, "Atrial fibrillation after coronary artery bypass surgery: A study of causes and risk factors," Acta Universitatis Upsaliensis, Uppsala, Sweden (2001)

Borovikova L V et al., "Vagus nerve stimulation attenuates the systemic inflammatory response to endotoxin," Nature 405(6785):458-62 (2000)

Wang H et al., "Nicotinic acetylcholine receptor alpha-7 subunit is an essential regulator of inflammation," Nature 421: 384-388 (2003)

Vanoli E et al., "Vagal stimulation and prevention of sudden death in conscious dogs with a healed myocardial infarction," Circ Res 68(5):1471-81 (1991)

De Ferrari G M, "Vagal reflexes and survival during acute myocardial ischemia in conscious dogs with healed myocardial infarction," Am J Physiol 261(1 Pt 2):H63-9 (1991)

Li D et al., "Promotion of Atrial Fibrillation by Heart Failure in Dogs: Atrial Remodeling of a Different Sort," Circulation 100(1):87-95 (1999)

Feliciano L et al., "Vagal nerve stimulation during muscarinic and beta-adrenergic blockade causes significant coronary artery dilation," Cardiovasc Res 40(1):45-55 (1998)

Carlson M D et al., "Selective stimulation of parasympathetic nerve fibers to the human sinoatrial node," Circulation 85:1311-1317 (1992)

Pagé P L et al., "Regional distribution of atrial electrical changes induced by stimulation of extracardiac and intracardiac neural elements," J Thorac Cardiovasc Surg 109 (2):377-88 (1995)

Masato Tsuboi et al., "Inotropic, chronotropic, and dromotropic effects mediated via parasympathetic ganglia in the dog heart," Am J Physiol Heart Circ Physiol 279: H1201-H1207 (2000)

Furukawa Y et al., "Differential blocking effects of atropine and gallamine on negative chronotropic and dromotropic responses to vagus stimulation in anesthetized dogs," J Pharmacol Exp Ther 251(3):797-802 (1989)

Bluemel K M, "Parasympathetic postganglionic pathways to the sinoatrial node," J Physiol 259(5 Pt 2):H1504-10 (1990)

Mazgalev T N, "AV Nodal Physiology," Heart Rhythm Society (www.hrsonline.org) (no date)

Bibevski S et al., "Ganglionic Mechanisms Contribute to Diminished Vagal Control in Heart Failure," Circulation 99:2958-2963 (1999)

Hirose M et al., "Pituitary Adenylate Cyclase-Activating Polypeptide-27 Causes a Biphasic Chronotropic Effect and Atrial Fibrillation in Autonomically Decentralized, Anesthetized Dogs," J Pharmacol Exp Ther 283(2):478-87 (1997)

Chen S A et al., "Intracardiac stimulation of human parasympathetic nerve fibers induces negative dromotropic effects: implication with the lesions of radiofrequency catheter ablation," J Cardiovasc Electrophysiol 9(3):245-52 (1998)

Cooper et al., "Neural effects on sinus rate and atrial ventricular conduction produced by electrical stimulation from a transvenous electrode catheter in the canine right pulmonary artery" Circ Res Vol. 46(1):48-57 (1980)

Kamath et al., "Effect of vagal nerve electrostimulation on the power spectrum of heart rate variability in man," Pacing Clin Electrophysiol 15:235-43 (1992)

Kleiger R E et al., "Decreased heart rate variability and its association with increased mortality after myocardial infarction," Am J Cardiol 59: 256-262 (1987)

Akselrod S et al., "Power spectrum analysis of heart rate fluctuation: a quantitative probe of beat-to-beat cardiovascular control," Science 213: 220-222 (1981)

A number of patents describe techniques for treating arrhythmias and/or ischemia by, at least in part, stimulating the vagus nerve. Arrhythmias in which the heart rate is too fast include fibrillation, flutter and tachycardia. Arrhythmia in which the heart rate is too slow is known as bradyarrhythmia. U.S. Pat. No. 5,700,282 to Zabara, which is incorporated herein by reference, describes techniques for stabilizing the heart rhythm of a patient by detecting arrhythmias and then electronically stimulating the vagus and cardiac sympathetic nerves of the patient. The stimulation of vagus efferents directly causes the heart rate to slow down, while the stimulation of cardiac sympathetic nerve efferents causes the heart rate to quicken.

The following patent and patent application publications, all of which are incorporated herein by reference, may be of interest:

U.S. Pat. No. 5,330,507 to Schwartz

European Patent Application EP 0 688 577 to Holmström et al.

U.S. Pat. Nos. 5,690,681 and 5,916,239 to Geddes et al.

US Patent Publication 2003/0229380 to Adams et al.

U.S. Pat. No. 6,511,500 to Rahme

U.S. Pat. No. 5,199,428 to Obel et al.

U.S. Pat. Nos. 5,334,221 to Bardy and 5,356,425 to Bardy et al.

U.S. Pat. No. 5,522,854 to Ideker et al.

U.S. Pat. No. 6,434,424 to Igel et al.

US Patent Application Publication 2002/0120304 to Mest

U.S. Pat. Nos. 6,006,134 and 6,266,564 to Hill et al.

PCT Publication WO 02/085448 to Foreman et al.

U.S. Pat. No. 5,243,980 to Mehra

U.S. Pat. No. 5,658,318 to Stroetmann et al.

U.S. Pat. No. 6,292,695 to Webster, Jr. et al.

U.S. Pat. No. 6,134,470 to Hartlaub

A number of patents and articles describe other methods and devices for stimulating nerves to achieve a desired effect. Often these techniques include a design for an electrode or electrode cuff.

The following patent and patent application publications, all of which are incorporated herein by reference, may be of interest:

US Patent Publication 2003/0050677 to Gross et al.

U.S. Pat. No. 4,608,985 to Crish et al.

U.S. Pat. No. 4,649,936 to Ungar et al.

PCT Patent Publication WO 01/10375 to Felsen et al.

U.S. Pat. No. 5,755,750 to Petruska et al.

U.S. Pat. No. 6,600,956 to Maschino et al.

The following articles, which are incorporated herein by reference, may be of interest:

Ungar I J et al., "Generation of unidirectionally propagating action potentials using a monopolar electrode cuff," Annals of Biomedical Engineering, 14:437-450 (1986)

Sweeney J D et al., "An asymmetric two electrode cuff for generation of unidirectionally propagated action potentials," IEEE Transactions on Biomedical Engineering, vol. BME-33(6) (1986)

Sweeney J D et al., "A nerve cuff technique for selective excitation of peripheral nerve trunk regions," IEEE Transactions on Biomedical Engineering, 37(7) (1990)

Naples G G et al., "A spiral nerve cuff electrode for peripheral nerve stimulation," by IEEE Transactions on Biomedical Engineering, 35(11) (1988)

van den Honert C et al., "Generation of unidirectionally propagated action potentials in a peripheral nerve by brief stimuli," Science, 206:1311-1312 (1979)

van den Honert C et al., "A technique for collision block of peripheral nerve: Single stimulus analysis," MP-11, IEEE Trans. Biomed. Eng. 28:373-378 (1981)

van den Honert C et al., "A technique for collision block of peripheral nerve: Frequency dependence," MP-12, IEEE Trans. Biomed. Eng. 28:379-382 (1981)

Rijkhoff N J et al., "Acute animal studies on the use of anodal block to reduce urethral resistance in sacral root stimulation," IEEE Transactions on Rehabilitation Engineering, 2(2):92 (1994)

Mushahwar V K et al., "Muscle recruitment through electrical stimulation of the lumbo-sacral spinal cord," IEEE Trans Rehabil Eng, 8(1):22-9 (2000)

Deurloo K E et al., "Transverse tripolar stimulation of peripheral nerve: a modelling study of spatial selectivity," Med Biol Eng Comput, 36(1):66-74 (1998)

Tarver W B et al., "Clinical experience with a helical bipolar stimulating lead," Pace, Vol. 15, October, Part II (1992)

Manfredi M, "Differential block of conduction of larger fibers in peripheral nerve by direct current," Arch. Ital. Biol., 108:52-71 (1970)

In physiological muscle contraction, nerve fibers are recruited in the order of increasing size, from smaller-diameter fibers to progressively larger-diameter fibers. In contrast, artificial electrical stimulation of nerves using standard techniques recruits fibers in a larger- to smaller-diameter order, because larger-diameter fibers have a lower excitation threshold. This unnatural recruitment order causes muscle fatigue and poor force gradation. Techniques have been explored to mimic the natural order of recruitment when performing artificial stimulation of nerves to stimulate muscles.

Fitzpatrick et al., in "A nerve cuff design for the selective activation and blocking of myelinated nerve fibers," Ann. Conf. of the IEEE Eng. in Medicine and Biology Soc, 13(2), 906 (1991), which is incorporated herein by reference, describe a tripolar electrode used for muscle control. The electrode includes a central cathode flanked on its opposite sides by two anodes. The central cathode generates action potentials in the motor nerve fiber by cathodic stimulation. One of the anodes produces a complete anodal block in one direction so that the action potential produced by the cathode is unidirectional. The other anode produces a selective anodal block to permit passage of the action potential in the opposite direction through selected motor nerve fibers to produce the desired muscle stimulation or suppression.

The following articles, patent publications, and patent application publications, all of which are incorporated herein by reference, may be of interest:

Rijkhoff N J et al., "Orderly recruitment of motoneurons in an acute rabbit model," Ann. Conf. of the IEEE Eng., Medicine and Biology Soc., 20(5):2564 (1998)

Rijkhoff N J et al., "Selective stimulation of small diameter nerve fibers in a mixed bundle," Proceedings of the Annual Project Meeting Sensations/Neuros and Mid-Term Review Meeting on the TMR-Network Neuros, Apr. 21-23, 1999, pp. 20-21 (1999)

Baratta R et al., "Orderly stimulation of skeletal muscle motor units with tripolar nerve cuff electrode," IEEE Transactions on Biomedical Engineering, 36(8):836-43 (1989)

Levy M N, Blattberg B., "Effect of vagal stimulation on the overflow of norepinephrine into the coronary sinus during sympathetic nerve stimulation in the dog," Circ Res 1976 February; 38(2):81-4

Lavallee et al. "Muscarinic inhibition of endogenous myocardial catecholamine liberation in the dog," Can J Physiol Pharmacol 1978 August; 56(4):642-9

Mann D L, Kent R L, Parsons B, Cooper G, "Adrenergic effects on the biology of the adult mammalian cardiocyte," Circulation 1992 February; 85(2):790-804

Mann D L, "Basic mechanisms of disease progression in the failing heart: role of excessive adrenergic drive," Prog Cardiovasc Dis 1998 July-August; 41(1 suppl 1):1-8

Barzilai A, Daily D, Zilkha-Falb R, Ziv I, Offen D, Melamed E, Sirv A, "The molecular mechanisms of dopamine toxicity," Adv Neurol 2003; 91:73-82

The following articles, which are incorporated herein by reference, describe techniques using point electrodes to selectively excite peripheral nerve fibers:

Grill W M et al., "Inversion of the current-distance relationship by transient depolarization," IEEE Trans Biomed Eng, 44(1):1-9 (1997)

Goodall E V et al., "Position-selective activation of peripheral nerve fibers with a cuff electrode," IEEE Trans Biomed Eng, 43(8):851-6 (1996)

Veraart C et al., "Selective control of muscle activation with a multipolar nerve cuff electrode," IEEE Trans Biomed Eng, 40(7):640-53 (1993)

U.S. Pat. No. 6,620,186 to Saphon et al.

U.S. Pat. No. 6,393,323 to Sawan et al.

U.S. Pat. No. 5,891,179 to Er et al.

U.S. Pat. No. 6,366,813 to DiLorenzo

US Patent Application Publication 2004/0172075 to Shafer et al.

U.S. Pat. No. 6,341,236 to Osorio et al.

SUMMARY OF THE INVENTION

In some embodiments of the present invention, a vagal stimulation system for treating a heart condition comprises a multipolar electrode device that is applied to a portion of a vagus nerve that innervates the heart of a subject. A control unit drives the electrode device to apply vagal stimulation, and configures the stimulation to minimize adverse pain, discomfort, or damage sometimes associated with vagal stimulation. Typically, the system is configured to treat heart failure and/or heart arrhythmia, such as atrial fibrillation or tachycardia.

In some embodiments of the present invention, the vagal stimulation system is configured to apply vagal stimulation in a series of bursts, at least one of which bursts includes a plurality of pulses. The control unit configures: (a) a pulse repetition interval (PRI) within each of the multi-pulse bursts (i.e., the time from the initiation of a pulse to the initiation of the following pulse within the same burst) to be on average at least 20 ms, such as at least 30 ms, e.g., at least 50 ms, and (b) the burst duration to be less than 75% of the interburst interval (i.e., the time from the initiation of a burst to the initiation of the following burst), such as less than 67% of the interburst interval, e.g., less than 50% or 33%. ("Burst duration," as used in the present application, including in the claims, is the time from the initiation of the first pulse within a burst to the conclusion of the last pulse within the burst.) In experiments conducted on human subjects, the inventors found that increasing the PRI of the applied stimulation reduced sensations of acute pain experienced by the subjects.

For some applications, the control unit is configured to synchronize the bursts with a feature of the cardiac cycle of the subject. For example, each of the bursts may commence after a delay after a detected R-wave, P-wave, or other feature of an ECG. Alternatively, for some applications, the control unit is configured to synchronize the bursts with other physiological activity of the subject, such as respiration, muscle contractions, or spontaneous nerve activity.

In some embodiments of the present invention, the control unit is configured to apply the vagal stimulation during "on" periods alternating with "off" periods, during which no stimulation is applied (each set of a single "on" period followed by a single "off" period is referred to hereinbelow as a "cycle"). Typically, each cycle has a duration of between about 10 seconds and about 10 minutes, such as between about 20 seconds and about 5 minutes, e.g., about 30 seconds. The control unit is further configured to apply such intermittent stimulation during stimulation periods alternating with rest periods, during which no stimulation is applied. Each of the rest periods typically has a duration equal to at least the duration of one cycle, e.g., between one and 50 cycles, such as between two and four cycles, and each of the stimulation periods typically has a duration equal to at least 5 times the rest period duration, such as at least 10 times, e.g., at least 15 times. For example, each of the stimulation periods may have a duration of at least 30 cycles, e.g., at least 60 cycles or at least 120 cycles, and no greater than 2400 cycles, e.g., no greater than 1200 cycles. Alternatively, the duration of the stimulation and rest periods are expressed in units of time, and each of the rest periods has a duration of at least 30 seconds, e.g., such as at least one minute, at least two minutes, at least 5 minutes, or at least 25 minutes, and each of the stimulation periods has a duration of at least 10 minutes, e.g., at least 30 minutes, such as at least one hour, and less than 12 hours, e.g., less than six hours, such as less than two hours.

In human experiments conducted by the inventors, it was observed that application of continuous intermittent stimulation (i.e., without providing the rest periods described above) for long periods of time (e.g., several hours or several days) sometimes causes neuropathic pain. Providing a rest period of several minutes duration once every several hours eliminated this neuropathic pain and prevented its recurrence.

In some embodiments of the present invention, the vagal stimulation system is configured to apply vagal stimulation in a series of bursts, each of which includes one or more pulses (pulses per trigger, or PPT). The control unit is configured to apply the vagal stimulation during "on" periods alternating with "off" periods, during which no stimulation is applied. At the commencement of each "on" period, the control unit ramps up the PPT of successive bursts, and at the conclusion of each "on" period, the control unit ramps down the PPT of successive bursts. For example, the first four bursts of an "on" period may have respective PPTs of 1, 2, 3, and 3, or 1, 2, 3, and 4, and the last four bursts of an "on" period may have respective PPTs of 3, 3, 2, and 1, or 4, 3, 2, and 1. Use of such ramping generally prevents or reduces sudden drops and rebounds in heart rate at the beginning and end of each "on" period, respectively. Such sudden drops and rebounds are particularly undesirable in subjects suffering from heart disease, such as heart failure.

For some applications, the control unit is configured to synchronize the bursts with a feature of the cardiac cycle of the subject. For example, each of the bursts may commence after a delay after a detected R-wave, P-wave, or other feature of an ECG. Alternatively, for some applications, the control unit is configured to synchronize the bursts with other physiological activity of the subject, such as respiration, muscle contractions, or spontaneous nerve activity. For some applications, such ramping is applied only at the commencement of each "on" period, or only at the conclusion of each "on" period, rather than during both transitional periods. For some applications, such ramping techniques are combined with the extended PRI techniques described hereinabove, and/or with the rest period techniques described hereinabove.

In some embodiments of the present invention, the control unit is configured to drive the electrode device to stimulate the vagus nerve so as to reduce the heart rate of the subject towards a target heart rate. Parameters of stimulation are varied in real time in order to vary the heart-rate-lowering effects of the stimulation. In embodiments of the present invention in which the stimulation is applied in a series of bursts that are synchronized with the cardiac cycle of the subject, such as described hereinabove, parameters of such bursts typically include, but are not limited to: (a) timing of the stimulation within the cardiac cycle, (b) pulse duration (width), (c) pulse repetition interval within each burst, (d) number of pulses per burst, also referred to herein as "pulses per trigger" (PPT), (e) amplitude, (f) duty cycle, (g) choice of vagus nerve, and (h) "on"/"off" ratio and timing (i.e., during intermittent operation). For some applications, the pulse repetition interval is maintained generally constant, while the PPT is varied to regulate the amount of stimulation applied to the vagus nerve.

In some embodiments of the present invention, the control unit is configured to gradually ramp the commencement and/or termination of stimulation. In order to achieve the gradual ramp, the control unit is typically configured to gradually modify one or more stimulation parameters, such as those described hereinabove, e.g., pulse amplitude, PPT, pulse frequency, pulse width, "on" time, and/or "off" time. As appropriate, one or more of these parameters are varied by less than 50% of a pre-termination value per heart beat, in order to achieve the gradual ramp. For example, stimulation at 5 PPT may be gradually terminated by reducing the PPT by 1 pulse per hour. Alternatively, one or more of the parameters are varied by less than 5% per heart beat, in order to achieve the gradual ramp. Terminating stimulation gradually, rather than suddenly, may reduce the likelihood of a rebound acceleration of heart rate that sometimes occurs upon termination of vagal stimulation. For some applications, the control unit is configured to gradually increase the strength of stimulation according to a predetermined schedule. Such a gradual increase is typically appropriate during the first several weeks, e.g., the first several days, of use of the stimulation system by a new subject, and/or when changing from one mode of operation to a different mode of operation. For example, the strength of stimulation may be increased less than 50% per hour, or less than 10% per day.

In some embodiments of the present invention, for applications in which the control unit is configured to apply vagal stimulation intermittently, as described hereinabove, the control unit begins the stimulation with an "off" period, rather than with an "on" period. As a result, a delay having the duration of an "off" period occurs prior to beginning stimulation. Alternatively or additionally, whether or not configured to apply stimulation intermittently, the control unit is configured to delay beginning the application of stimulation for a certain time period after receiving an external command to apply the stimulation. For some applications, the length of the time period is determined responsive to the output of a pseudo-random number generator. The use of these delaying techniques generally reduces a subject's anticipation of any discomfort that he may associate with stimulation, and disassociates the sensations of stimulation from the physician and/or an external control device such as a wand.

"Vagus nerve," and derivatives thereof, as used in the specification and the claims, is to be understood to include portions of the left vagus nerve, the right vagus nerve, and branches of the vagus nerve such as the superior cardiac nerve, superior cardiac branch, and inferior cardiac branch. Similarly, stimulation of the vagus nerve is described herein by way of illustration and not limitation, and it is to be understood that stimulation of other autonomic nerves, including nerves in the epicardial fat pads, for treatment of heart conditions or other conditions, is also included within the scope of the present invention.

"Heart failure," as used in the specification and the claims, is to be understood to include all forms of heart failure, including ischemic heart failure, non-ischemic heart failure, and diastolic heart failure.

There is therefore provided, in accordance with an embodiment of the present invention, an electrode device, configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein; and a control unit, configured to:
drive the electrode device to apply to the site a current in at least first and second bursts, the first burst including a plurality of pulses, and the second burst including at least one pulse, and set (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

In an embodiment, the control unit is configured to set the percentage to be less than 50%, such as less than 33%.

For some applications, the control unit is configured to set the average PRI of the first burst to be less than 200 ms. For some applications, the control unit is configured to set the interburst interval to be between 400 ms and 1500 ms.

For some applications, the control unit is configured to configure the first burst to include at least three pulses. Alternatively or additionally, the control unit is configured to set the first burst to include no more than six pulses.

For some applications, the control unit is configured to set an average duration of the pulses of the first burst to be less than 4 ms.

In an embodiment, the site includes the vagus nerve, and the electrode device is configured to be coupled to the vagus nerve.

For some applications, the control unit is configured to set the first burst to include a desired number of the pulses, and set the average PRI to be at least 75% of a maximum PRI possible given the interburst interval, the percentage, and the desired number of the pulses, but, in any event, no greater than 225 ms.

For some applications, the control unit is configured to withhold applying the current to the site when the pulses of the first and second bursts are not being applied.

For some applications, the control unit is configured to:
drive the electrode device to apply the current in at least the first and the second bursts, and in at least a third burst following the second burst, wherein the second burst includes a plurality of pulses, and wherein the third burst includes at least one pulse, and set (a) a PRI of the second burst to be on average at least 20 ms, (b) an interburst interval between initiation of the second burst and initiation of the third burst to be less than 10 seconds, (c) an interburst gap between a conclusion of the second burst and the initiation of the third burst to have a duration greater than the average PRI of the second burst, and (d) a burst duration of the second burst to be less than 67% of the interburst interval between the initiation of the second burst and initiation of the third burst.

For some applications, the control unit is configured to set the average PRI to be at least 30 ms, or at least 50 ms.

For some applications, the control unit is configured to apply an interburst current to the site during at least a portion of the interburst gap, and to set the interburst current on average to be less than 50% of the current applied on average during the first burst. For some applications, the control unit is configured to apply an interburst current to the site during at least a portion of the interburst gap, and to set the interburst current on average to be less than 20% of the current applied on average during the first burst, such as less than 5% of the current applied on average during the pulses.

In an embodiment, the control unit is configured to:
drive the electrode device to apply the current during "on" periods that alternate with low stimulation periods, at least one of the "on" periods having an "on" duration of at least three seconds, and including at least three bursts, and at least one of the low stimulation periods immediately following the at least one of the "on" periods having a low stimulation duration equal to at least 50% of the "on" duration, wherein the at least three bursts of the at least one of the "on" periods include the first and second bursts, set the current applied on average during the low stimulation periods to be less than 50% of the current applied on average during the "on" periods, and during at least one transitional period of at the least one of the "on" periods, ramp a number of pulses per burst, the at least one transitional period selected from the group consisting of: a commencement of the at least one of the "on" periods, and a conclusion of the at least one of the "on" periods.

For some applications, the control unit is configured to set the current applied on average during the low stimulation periods to be less than 20% of the current applied on average during the "on" periods, such as less than 5% of the current applied on average during the "on" periods. For some applications, the control unit is configured to withhold applying the current during the low stimulation periods.

In an embodiment, the control unit is configured to:
drive the electrode device, during stimulation periods alternating with rest periods, to apply the current during "on" periods that alternate with low stimulation periods, the "on" periods having on average an "on" duration equal to at least 1 second, and the low stimulation periods having on average a low stimulation duration equal to at least 50% of the "on" duration, wherein at least one of the "on" periods includes the first and second bursts, set the current applied on average during the low stimulation periods to be less than 20% of the current applied on average during the "on" periods, and set the current applied on average during the rest periods to be less than 20% of the current applied on average during the "on" periods, wherein the rest periods have on average a rest period duration equal to at least a cycle duration that equals a duration of a single "on" period plus a duration of a single low stimulation period, and wherein the stimulation periods have on average a stimulation period duration equal to at least five times the rest period duration.

For some applications, the control unit is configured to set the current applied on average during the low stimulation periods to be less than 5% of the current applied on average during the "on" periods, and to set the current applied on average during the rest periods to be less than 5% of the current applied on average during the "on" periods. For some applications, the control unit is configured to withhold applying the current during the low stimulation periods and during the rest periods.

In an embodiment, the control unit is configured to set the first burst to include a desired number of the pulses, and set the average PRI to be at least 75% of a maximum PRI possible given the interburst interval, the percentage, and the desired number of the pulses. For some applications, the control unit is configured to set the average PRI to be at least 75% of (a) the interburst interval times (b) the percentage divided by (c) the difference between (i) the desired number of the pulses and (ii) one.

For some applications, the control unit is configured to set the average PRI of the first burst to be at least 30 ms, such as at least 50 ms, or at least 75 ms.

In an embodiment, the apparatus includes a sensor configured to sense a physiological parameter of the subject indicative of physiological activity of the subject, and the control unit is configured to synchronize the first and second bursts with the physiological activity. For some applications, the physiological activity is selected from the group consisting of: respiration of the subject, muscle contractions of the subject, and spontaneous nerve activity of the subject, and the sensor is configured to sense the physiological parameter indicative of the selected physiological activity. For some applications, the physiological activity includes cardiac activity of the subject, and the control unit is configured to synchronize the first and second bursts with a feature of a cardiac cycle of the subject. For example, the control unit may be configured to set the interburst interval to be equal to a sum of one or more sequential R-R intervals of the subject.

There is further provided, in accordance with an embodiment of the present invention, apparatus including:

an electrode device, configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein; and a control unit, configured to:
  drive the electrode device, during stimulation periods that alternate with rest periods, to apply to the site a current during "on" periods that alternate with low stimulation periods, the "on" periods having on average an "on" duration equal to at least 1 second, and the low stimulation periods having on average a low stimulation duration equal to at least 50% of the "on" duration,
  set the current applied on average during the low stimulation periods to be less than 20% of the current applied on average during the "on" periods, and
  set the current applied on average during the rest periods to be less than 20% of the current applied on average during the "on" periods, wherein the rest periods have on average a rest period duration equal to at least a cycle duration that equals a duration of a single "on" period plus a duration of a single low stimulation period, and wherein the stimulation periods have on average a stimulation period duration equal to at least five times the rest period duration.

For some applications, the control unit is configured to set the low stimulation duration to be at least 100% of the "on" duration. For some applications, the control unit is configured to set the rest period duration to be on average at least two times the cycle duration. For some applications, the control unit is configured to set the rest period duration to be on average at least 30 seconds.

For some applications, the control unit is configured to set the "on" duration to be on average at least 5 seconds.

For some applications, the control unit is configured to set the stimulation period duration to be on average at least 30 times the cycle duration. For some applications, the control unit is configured to set the stimulation period duration to be on average at least 30 minutes.

For some applications, the control unit is configured to:
  drive the electrode device, during at least one of the "on" periods, to apply the current in at least first and second bursts, the first burst including a plurality of pulses, and the second burst including at least one pulse, and
  set (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

For some applications, the control unit is configured to:
  set the "on" duration of at least one of the "on" periods to be at least three seconds,
  configure the at least one of the "on" periods to include at least three bursts,
  during at least one transitional period of the at least one of the "on" periods, ramp a number of pulses per burst, the at least one transitional period selected from the group consisting of: a commencement of the at least one of the "on" periods, and a conclusion of the at least one of the "on" periods.

For some applications, the control unit is configured to set the low stimulation duration to be less than 5 times the "on" duration.

For some applications, the control unit is configured to set the stimulation period duration to be on average at least 10 times the rest period duration, such as at least 15 times the rest period duration.

For some applications, the control unit is configured to set the current applied on average during the low stimulation periods to be less than 20% of the current applied on average during the "on" periods, and to set the current applied on average during the rest periods to be less than 20% of the current applied on average during the "on" periods. For example, the control unit may be configured to set the current applied on average during the low stimulation periods to be less than 5% of the current applied on average during the "on" periods, and to set the current applied on average during the rest periods to be less than 5% of the current applied on average during the "on" periods. For some applications, the control unit is configured to withhold applying the current during the low stimulation periods and during the rest periods.

In an embodiment, the control unit is configured to:

drive the electrode device to apply the current at least intermittently to the site for at least three hours, which at least three hours includes a period having a duration of three hours, which period is divided into a number of equal-duration sub-periods such that each of the sub-periods has a sub-period duration equal to three hours divided by the number, wherein the number is between 5 and 10, configure the current to cause, during at least 20% of each of the sub-periods, an average reduction of at least 5% in a heart rate of the subject compared to a baseline heart rate of the subject, and configure the current to not cause secondary neuropathic pain.

In an embodiment, the site includes the vagus nerve, and the electrode device is configured to be coupled to the vagus nerve.

In an embodiment, the control unit is configured to:

drive the electrode device to apply the current at least intermittently to the vagus nerve for at least three hours, which at least three hours includes a period having a duration of three hours, configure the stimulation to include at least 3000 pulses during the period, the pulses having on average a pulse duration of at least 0.5 ms, configure the stimulation to cause, on average during the pulses, at least 3 mA to enter tissue of the vagus nerve, and configure the stimulation to not cause secondary neuropathic pain.

There is still further provided, in accordance with an embodiment of the present invention, apparatus including:

an electrode device, configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein; and a control unit, configured to:

drive the electrode device to apply to the site a current in bursts of one or more pulses, during "on" periods that alternate with low stimulation periods, wherein at least one of the "on" periods has an "on" duration of at least three seconds, and including at least three bursts, and wherein at least one of the low stimulation periods immediately following the at least one of the "on" periods has a low stimulation duration equal to at least 50% of the "on" duration, set the current applied on average during the low stimulation periods to be less than 20% of the current applied on average during the "on" periods, and during at least one transitional period of the at least one of the "on" periods, ramp a number of pulses per burst, the at least one transitional period selected from the group consisting of: a commencement of the at least one of the "on" periods, and a conclusion of the at least one of the "on" periods.

For some applications, the control unit is configured to set the one or more pulses to have a characteristic pulse duration, at least one of the number of pulses includes a non-integer portion, and the control unit is configured to drive the electrode device to apply the non-integer portion by applying a pulse having a duration less than the characteristic pulse duration.

In an embodiment, the apparatus includes a sensor configured to sense a physiological parameter of the subject indicative of physiological activity of the subject, and the control unit is configured to synchronize the bursts with the physiological activity. For some applications, the physiological activity is selected from the group consisting of: respiration of the subject, muscle contractions of the subject, and spontaneous nerve activity of the subject, and the sensor is configured to sense the physiological parameter indicative of the selected physiological activity. For some applications, the physiological activity includes cardiac activity of the subject, and the control unit is configured to synchronize the bursts with a feature of a cardiac cycle of the subject. For example, the control unit may be configured to set the at least one of the "on" periods to include at least 10 bursts.

In an embodiment, the control unit is configured to:

drive the electrode device, during the at least one of the "on" periods, to apply the current in at least first and second bursts, the first burst including a plurality of pulses, and the second burst including at least one pulse, and set (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

For some applications, the control unit is configured to set the low stimulation duration of the at least one of the low stimulation periods immediately following the at least one of the "on" periods to be less than 5 times the "on" duration.

In an embodiment, the site includes the vagus nerve, and the electrode device is configured to be coupled to the vagus nerve.

In an embodiment, the control unit is configured to drive the electrode device to apply the current during stimulation periods alternating with rest periods, and to set the current applied on average during the rest periods to be less than 50% of the current applied on average during the "on" periods, wherein the rest periods have on average a rest period duration equal to at least a cycle duration that equals a duration of a single "on" period plus a duration of a single low stimulation period, and wherein the stimulation periods have on average a stimulation period duration equal to at least five times the rest period duration. For some applications, the control unit is configured to set the current applied on average during the rest periods to be less than 20% of the current applied on average during the "on" periods, such as less than 5% of the current applied on average during the "on" periods. For some applications, the control unit is configured to withhold applying the current during the rest periods.

For some applications, the at least one transitional period includes the commencement of the at least one of the "on" periods, and the control unit is configured to ramp up the number of pulses per burst during the commencement. For some applications, the control unit is configured to set the number of pulses of an initial burst of the at least one of the "on" periods and a second burst immediately subsequent to the initial burst to be equal to 1 and 2, respectively. For some applications, the control unit is configured to set the number of pulses of a third burst of the at least one of the "on" periods immediately subsequent to the second burst to be equal to 3.

For some applications, the at least one transitional period includes the conclusion of the at least one of the "on" periods, and the control unit is configured to ramp down the number of pulses per burst during the conclusion. For some applications, the control unit is configured to set the number of pulses of last and penultimate bursts of the at least one of the "on" periods to be equal to 1 and 2, respectively. For some applications, the control unit is configured to set the number of pulses of an antepenultimate burst of the at least one of the "on" periods to be equal to 3.

For some applications, the control unit is configured to set the current applied on average during the low stimulation periods to be less than 20% of the current applied on average during the "on" periods, such as less than 5% of the current applied on average during the "on" periods. For some applications, the control unit is configured to withhold applying the current during the low stimulation periods.

There is additionally provided, in accordance with an embodiment of the present invention, apparatus including:

an electrode device, configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein; and a control unit, configured to:

drive the electrode device to apply electrical stimulation to the site for at least three hours, which at least three hours includes a period having a duration of three hours, which period is divided into a number of equal-duration sub-periods such that each of the sub-periods has a sub-period duration equal to three hours divided by the number, wherein the number is between 5 and 10, configure the stimulation to cause, during at least 20% of each of the sub-periods, an average reduction of at least 5% in a heart rate of the subject compared to a baseline heart rate of the subject, and configure the stimulation to not cause secondary neuropathic pain.

In an embodiment, the control unit is configured to configure the stimulation to not cause local pain in a vicinity of the site.

For some applications, the control unit is configured to configure the stimulation to cause the average reduction during at least 40% of each of the sub-periods.

For some applications, the number of sub-periods is 6, such that the sub-period duration equals 30 minutes. Alternatively, for some applications, the number of sub-periods is 9, such that the sub-period duration equals 20 minutes.

In an embodiment, the site includes the vagus nerve, and the electrode device is configured to be coupled to the vagus nerve.

There is yet additionally provided, in accordance with an embodiment of the present invention, apparatus including:

an electrode device, configured to be coupled to a site of a vagus nerve of a subject; and a control unit, configured to:

drive the electrode device to apply electrical stimulation to the site for at least three hours, which at least three hours includes a period having a duration of three hours, configure the stimulation to include at least 3000 pulses during the period, the pulses having on average a pulse duration of at least 0.5 ms, configure the stimulation to cause, on average during the pulses, at least 3 mA to enter tissue of the vagus nerve, and configure the stimulation to not cause secondary neuropathic pain.

In an embodiment, the control unit is configured to configure the stimulation to not cause local pain in a vicinity of the site.

For some applications, the control unit is configured to configure the stimulation to include at least 5000 pulses during the period. For some applications, the control unit is configured to configure the stimulation to cause, on average during the pulses, at least 4 mA to enter the tissue of the vagus nerve. For some applications, the control unit is configured to set the pulse duration to be at least 0.9 ms.

There is also provided, in accordance with an embodiment of the present invention, apparatus including:

an electrode device, configured to be coupled to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein;

a sensor configured to sense a physiological parameter of the subject indicative of physiological activity of the subject; and a control unit, configured to:

drive the electrode device to apply to the site a current in at least first and second bursts, the first burst including a plurality of pulses, and the second burst including at least one pulse, set a pulse repetition interval (PRI) of the first burst to be on average at least 20 ms, and synchronize the first and second bursts with the physiological activity.

For some applications, the physiological activity is selected from the group consisting of: respiration of the subject, muscle contractions of the subject, and spontaneous nerve activity of the subject, and the sensor is configured to sense the physiological parameter indicative of the selected physiological activity.

In an embodiment, the physiological activity includes cardiac activity of the subject, and the control unit is configured to synchronize the first and second bursts with a feature of a cardiac cycle of the subject. For some applications, the control unit is configured to set an interburst interval between initiation of the first burst and initiation of the second burst to be equal to a sum of one or more sequential R-R intervals of the subject.

In an embodiment, the site includes the vagus nerve, and the electrode device is configured to be coupled to the vagus nerve.

For some applications, the control unit is configured to set an interburst interval between initiation of the first burst and initiation of the second burst to be less than 10 seconds. Alternatively or additionally, the control unit is configured to set an interburst gap between a conclusion of the first burst and the initiation of the second burst to have a duration greater than the average PRI. Further alternatively or additionally, the control unit is configured to set a burst duration of the first burst to be less than a percentage of an interburst interval between initiation of the first burst and initiation of the second burst, the percentage being less than 67%.

There is also provided, in accordance with an embodiment of the present invention, a method including:

applying, to a site of a subject, a current in at least first and second bursts, the first burst including a plurality of pulses, and the second burst including at least one pulse, the site selected from the group consisting of: a vagus nerve, an epicardial fat pad, a pulmonary vein, a carotid artery, a carotid sinus, a coronary sinus, a vena cava vein, a right ventricle, a right atrium, and a jugular vein; and setting (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

There is further provided, in accordance with an embodiment of the present invention, a method including:

applying, to a site of a subject, during stimulation periods that alternate with rest periods, a current during "on" periods that alternate with low stimulation periods, the "on" periods having on average an "on" duration equal to at least 1 second, and the low stimulation periods having on average a low stimulation duration equal to at least 50% of the "on" duration, the site selected from the group consisting of: a vagus nerve, an epicardial fat pad, a pulmonary vein, a carotid artery, a carotid sinus, a coronary sinus, a vena cava vein, a right ventricle, a right atrium, and a jugular vein;

setting the current applied on average during the low stimulation periods to be less than 20% of the current applied on average during the "on" periods;

setting the current applied on average during the rest periods to be less than 20% of the current applied on average during the "on" periods; and setting the rest periods to have on average a rest period duration equal to at least a cycle duration that equals a duration of a single "on" period plus a duration of a single low stimulation period, and the stimulation periods to have on average a stimulation period duration equal to at least five times the rest period duration.

There is still further provided, in accordance with an embodiment of the present invention, a method including:

applying, to a site of a subject, a current in bursts of one or more pulses, during "on" periods that alternate with low stimulation periods, at least one of the "on" periods having an "on" duration of at least three seconds, and including at least three bursts, and at least one of the low stimulation periods immediately following the at least one of the "on" periods having a low stimulation duration equal to at least 50% of the "on" duration, the site selected from the group consisting of: a vagus nerve, an epicardial fat pad, a pulmonary vein, a carotid artery, a carotid sinus, a coronary sinus, a vena cava vein, a right ventricle, a right atrium, and a jugular vein;

setting the current applied on average during the low stimulation periods to be less than 20% of the current applied on average during the "on" periods; and during at least one transitional period of the at least one of the "on" periods, ramping a number of pulses per burst, the at least one transitional period selected from the group consisting of: a commencement of the at least one of the "on" periods, and a conclusion of the at least one of the "on" periods.

There is additionally provided, in accordance with an embodiment of the present invention, a method including:

applying electrical stimulation to a site of a subject for at least three hours, which at least three hours includes a period having a duration of three hours, which period is divided into a number of equal-duration sub-periods such that each of the sub-periods has a sub-period duration equal to three hours divided by the number, wherein the number is between 5 and 10, wherein the site is selected from the group consisting of: a vagus nerve, an epicardial fat pad, a pulmonary vein, a carotid artery, a carotid sinus, a coronary sinus, a vena cava vein, a right ventricle, a right atrium, and a jugular vein;

configuring the stimulation to cause, during at least 20% of each of the sub-periods, an average reduction of at least 5% in a heart rate of the subject compared to a baseline heart rate of the subject; and configuring the stimulation to not cause secondary neuropathic pain.

There is yet additionally provided, in accordance with an embodiment of the present invention, a method including:

applying electrical stimulation to a site of vagus nerve of a subject for at least three hours, which at least three hours includes a period having a duration of three hours;

configuring the stimulation to include at least 3000 pulses during the period, the pulses having on average a pulse duration of at least 0.5 ms;

configuring the stimulation to cause, on average during the pulses, at least 3 mA to enter tissue of the vagus nerve; and configuring the stimulation to not cause secondary neuropathic pain.

There is also provided, in accordance with an embodiment of the present invention, apparatus including:

an electrode device, configured to be coupled to tissue of a subject selected; and a control unit, configured to:

drive the electrode device to apply to the tissue a current in at least first and second bursts, the first burst including a plurality of pulses, and the second burst including at least one pulse, and set (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

For some applications, the tissue includes nerve tissue of the subject, and the electrode device is configured to be coupled to the nerve tissue. For some applications, the tissue includes muscle tissue of the subject, and the electrode device is configured to be coupled to the muscle tissue.

For some applications, the electrode device is configured to be implantable in a body of the subject.

There is further provided, in accordance with an embodiment of the present invention, apparatus including:

an electrode device, configured to be coupled to tissue of a subject; and a control unit, configured to:

drive the electrode device, during stimulation periods that alternate with rest periods, to apply to the tissue a current during "on" periods that alternate with low stimulation periods, the "on" periods having on average an "on" duration equal to at least 1 second, and the low stimulation periods having on average a low stimulation duration equal to at least 50% of the "on" duration, set the current applied on average during the low stimulation periods to be less than 20% of the current applied on average during the "on" periods, and set the current applied on average during the rest periods to be less than 20% of the current applied on average during the "on" periods, wherein the rest periods have on average a rest period duration equal to at least a cycle duration that equals a duration of a single "on" period plus a duration of a single low stimulation period, and wherein the stimulation periods have on average a stimulation period duration equal to at least five times the rest period duration.

For some applications, the tissue includes nerve tissue of the subject, and the electrode device is configured to be coupled to the nerve tissue. For some applications, the tissue includes muscle tissue of the subject, and the electrode device is configured to be coupled to the muscle tissue.

For some applications, the electrode device is configured to be implantable in a body of the subject.

There is also provided, in accordance with an embodiment of the present invention, a method including:

applying, to a site of a subject, a current in at least first and second bursts, the first burst including a plurality of pulses, and the second burst including at least one pulse, the site selected from the group consisting of: a vagus nerve, an epicardial fat pad, a pulmonary vein, a carotid artery, a carotid sinus, a coronary sinus, a vena cava vein, a right ventricle, a right atrium, and a jugular vein;

setting (a) a pulse repetition interval (PRI) of the first burst to be on average at least 20 ms;

sensing a physiological parameter of the subject indicative of physiological activity of the subject; and synchronizing the first and second bursts with the physiological activity.

There is still further provided, in accordance with an embodiment of the present invention, a method including:

applying, to tissue of a subject, a current in at least first and second bursts, the first burst including a plurality of pulses, and the second burst including at least one pulse; and setting (a) a pulse repetition interval (PRI) of the first burst to be on average at least 20 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

There is additionally provided, in accordance with an embodiment of the present invention, a method including:

applying, to tissue of a subject, during stimulation periods that alternate with rest periods, a current during "on" periods that alternate with low stimulation periods, the "on" periods having on average an "on" duration equal to at least 1 second, and the low stimulation periods having on average a low stimulation duration equal to at least 50% of the "on" duration;

setting the current applied on average during the low stimulation periods to be less than 20% of the current applied on average during the "on" periods;

setting the current applied on average during the rest periods to be less than 20% of the current applied on average during the "on" periods; and setting the rest periods to have on average a rest period duration equal to at least a cycle duration that equals a duration of a single "on" period plus a duration of a single low stimulation period, and the stimulation periods to have on average a stimulation period duration equal to at least five times the rest period duration.

The present invention will be more fully understood from the following detailed description of embodiments thereof, taken together with the drawings, in which:

BRIEF DESCRIPTION OF THE DRAWINGS

FIG. 2A is a simplified cross-sectional illustration of a multipolar electrode device applied to a vagus nerve, in accordance with an embodiment of the present invention;

FIG. 2B is a simplified cross-sectional illustration of a generally-cylindrical electrode device applied to a vagus nerve, in accordance with an embodiment of the present invention;

FIG. 2C is a simplified perspective illustration of the electrode device of FIG. 2A, in accordance with an embodiment of the present invention;

FIG. 3 is a conceptual illustration of the application of current to a vagus nerve, in accordance with an embodiment of the present invention;

DETAILED DESCRIPTION OF EMBODIMENTS

Figure 1:
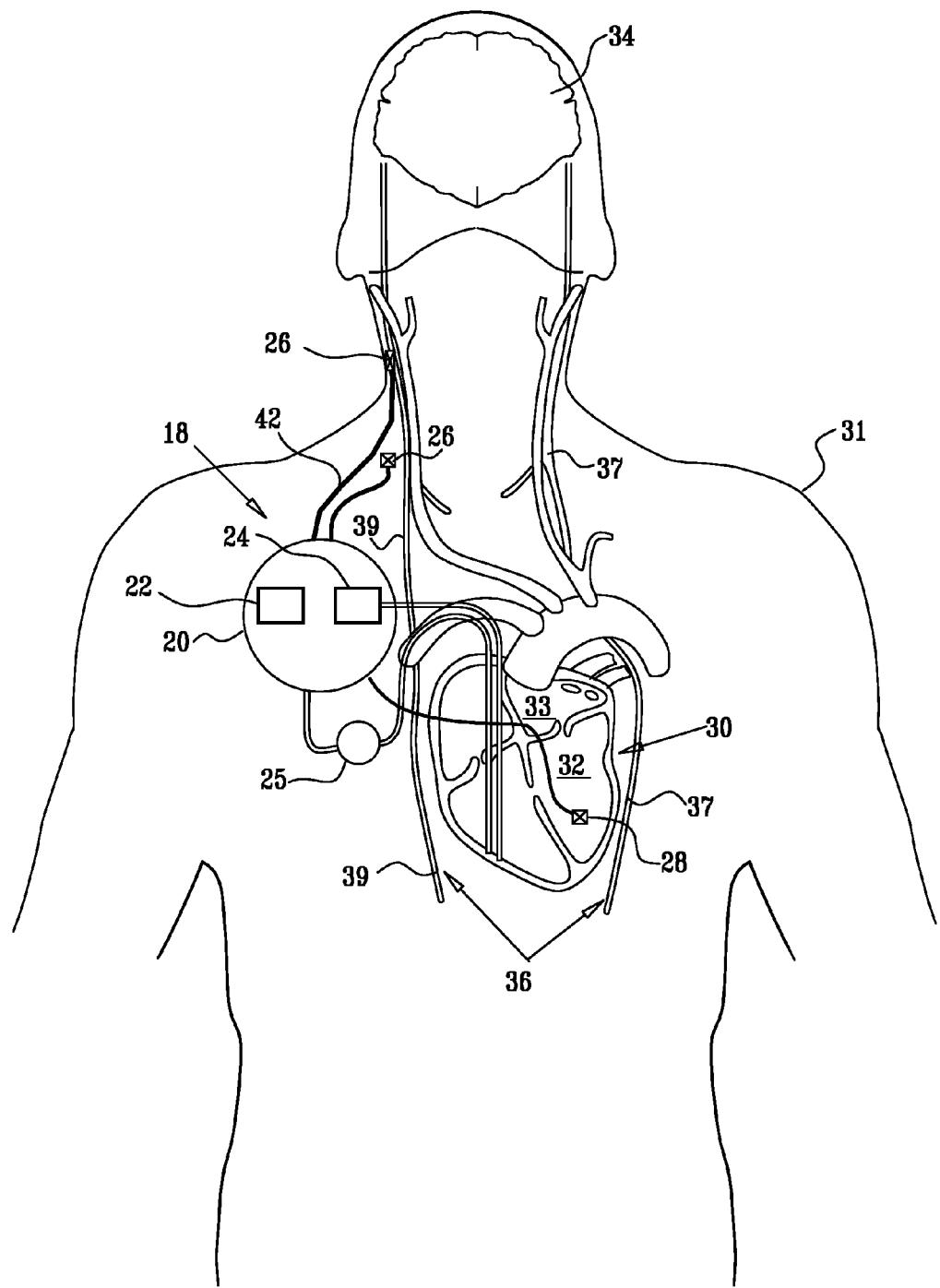
FIG. 1 is a block diagram that schematically illustrates a vagal stimulation system applied to a vagus nerve of a subject, in accordance with an embodiment of the present invention.

FIG. 1 is a block diagram that schematically illustrates a vagal stimulation system 18 comprising a multipolar electrode device 26, in accordance with an embodiment of the present invention. Electrode device 26 is applied to a portion of a vagus nerve 36 (a left vagus nerve 37 and/or a right vagus nerve 39), which innervates a heart 30 of a subject 31. Alternatively, electrode device 26 is applied to an epicardial fat pad, a pulmonary vein, a carotid artery, a carotid sinus, a coronary sinus, a vena cava vein, a right ventricle, a right atrium, or a jugular vein (configurations not shown). Typically, system 18 is utilized for treating a heart condition such as heart failure and/or cardiac arrhythmia. Vagal stimulation system 18 further comprises an implantable or external control unit 20, which typically communicates with electrode device 26 over a set of leads 42. Typically, control unit 20 drives electrode device 26 to (i) apply signals to induce the propagation of efferent nerve impulses towards heart 30, and (ii) suppress artificially-induced afferent nerve impulses towards a brain 34 of the subject, in order to minimize unintended side effects of the signal application. The efferent nerve pulses in vagus nerve 36 are typically induced by electrode device 26 in order to regulate the heart rate of the subject.

For some applications, control unit 20 is adapted to receive feedback from one or more of the electrodes in electrode device 26, and to regulate the signals applied to the electrode device responsive thereto.

Control unit 20 is typically adapted to receive and analyze one or more sensed physiological parameters or other parameters of the subject, such as heart rate, electrocardiogram (ECG), blood pressure, indicators of decreased cardiac contractility, cardiac output, norepinephrine concentration, left ventricular end diastolic pressure (LVEDP), or motion of the subject. In order to receive these sensed parameters, control unit 20 may comprise, for example, an ECG monitor 24, connected to a site on the subject's body such as heart 30, for example using one or more subcutaneous sensors or ventricular and/or atrial intracardiac sensors. The control unit may also comprise an accelerometer 22 for detecting motion of the subject. Alternatively, ECG monitor 24 and/or accelerometer 22 comprise separate implanted devices placed external to control unit 20, and, optionally, external to the subject's body. Alternatively or additionally, control unit 20 receives signals from one or more physiological sensors 28, such as blood pressure sensors. Sensors 28 are typically implanted in the subject, for example in a left ventricle 32 of heart 30. For example, sensors 28 may comprise a pressure gauge for measuring LVEDP, which gauge may be adapted to be placed in left ventricle 32, a left atrium 33 of heart 30, or in a pulmonary artery.

FIG. 2A is a simplified cross-sectional illustration of a generally-cylindrical electrode device 40 applied to vagus nerve 36, in accordance with an embodiment of the present invention. For some applications, electrode device 26 (FIG. 1) comprises electrode device 40. Alternatively, electrode device 26 comprises an electrode device known in the art of nerve stimulation, such as those described in some of the references incorporated herein by reference. Electrode device 40 comprises a central cathode 46 for applying a negative current ("cathodic current") in order to stimulate vagus nerve 36, as described below. Electrode device 40 additionally comprises a set of one or more anodes 44 (44a, 44b, herein: "efferent anode set 44"), placed between cathode 46 and the edge of electrode device 40 closer to heart 30 (the "efferent edge"). Efferent anode set 44 applies a positive current ("efferent anodal current") to vagus nerve 36, for blocking action potential conduction in vagus nerve 36 induced by the cathodic current, as described below. Typically, electrode device 40 comprises an additional set of one or more anodes 45 (45a, 45b, herein: "afferent anode set 45"), placed between cathode 46 and the edge of electrode device 40 closer to brain 34. Afferent anode set 45 applies a positive current ("afferent anodal current") to vagus nerve 36, in order to block propagation of action potentials in the direction of the brain during application of the cathodic current.

For some applications, the one or more anodes of efferent anode set 44 are directly electrically coupled to the one or more anodes of afferent anode set 45, such as by a common wire or shorted wires providing current to both anode sets substantially without any intermediary elements. Typically, coatings on the anodes, shapes of the anodes, positions of the anodes, sizes of the anodes and/or distances of the various anodes from the nerve are regulated so as to produce desired ratios of currents and/or desired activation functions delivered through or caused by the various anodes. For example, by varying one or more of these characteristics, the relative impedance between the respective anodes and central cathode 46 is regulated, whereupon more anodal current is driven through the one or more anodes having lower relative impedance. In these applications, central cathode 46 is typically placed closer to one of the anode sets than to the other, for example, so as to induce asymmetric stimulation (i.e., not necessarily unidirectional in all fibers) between the two sides of the electrode device. The closer anode set typically induces a stronger blockade of the cathodic stimulation.

Reference is now made to FIG. 2B, which is a simplified cross-sectional illustration of a generally-cylindrical electrode device 240 applied to vagus nerve 36, in accordance with an embodiment of the present invention. Electrode device 240 comprises exactly one efferent anode 244 and exactly one afferent anode 245, which are electrically coupled to each other, such as by a common wire 250 or shorted wires providing current to both anodes 244 and 245, substantially without any intermediary elements. The cathodic current is applied by a cathode 246 with an amplitude sufficient to induce action potentials in large- and medium-diameter fibers (e.g., A- and B-fibers), but insufficient to induce action potentials in small-diameter fibers (e.g., C-fibers).

Reference is again made to FIG. 2A. Cathodes 46 and anode sets 44 and 45 (collectively, "electrodes") are typically mounted in an electrically-insulating cuff 48 and separated from one another by insulating elements such as protrusions 49 of the cuff. Typically, the width of the electrodes is between about 0.5 and about 2 millimeters, or is equal to approximately one-half the radius of the vagus nerve. The electrodes are typically recessed so as not to come in direct contact with vagus nerve 36. For some applications, such recessing enables the electrodes to achieve generally uniform field distributions of the generated currents and/or generally uniform values of the activation function defined by the electric potential field in the vicinity of vagus nerve 24. Alternatively or additionally, protrusions 49 allow vagus nerve 24 to swell into the canals defined by the protrusions, while still holding the vagus nerve centered within cuff 48 and maintaining a rigid electrode geometry. For some applications, cuff 48 comprises additional recesses separated by protrusions, which recesses do not contain active electrodes. Such additional recesses accommodate swelling of vagus nerve 24 without increasing the contact area between the vagus nerve and the electrodes.

For some applications, the distance between the electrodes and the axis of the vagus nerve is between about 1 and about 4 millimeters, and is greater than the closest distance from the ends of the protrusions to the axis of the vagus nerve. Typically, protrusions 49 are relatively short (as shown). For some applications, the distance between the ends of protrusions 49 and the center of the vagus nerve is between about 1 and 3 millimeters. (Generally, the diameter of the vagus nerve is between about 2 and 3 millimeters.) Alternatively, for some applications, protrusions 49 are longer and/or the electrodes are placed closer to the vagus nerve in order to reduce the energy consumption of electrode device 40.

In an embodiment of the present invention, efferent anode set 44 comprises a plurality of anodes 44, typically two anodes 44a and 44b, spaced approximately 0.5 to 2.0 millimeters apart. Application of the efferent anodal current in appropriate ratios from a plurality of anodes generally minimizes the "virtual cathode effect," whereby application of too large an anodal current stimulates rather than blocks fibers. In an embodiment, anode 44a applies a current with an amplitude equal to about 0.5 to about 5 milliamps (typically one-third of the amplitude of the current applied by anode 44b). When such techniques are not used, the virtual cathode effect generally hinders blocking of smaller-diameter fibers, as described below, because a relatively large anodal current is generally necessary to block such fibers.

Anode 44a is typically positioned in cuff 48 to apply current at the location on vagus nerve 36 where the virtual cathode effect is maximally generated by anode 44b. For applications in which the blocking current through anode 44b is expected to vary substantially, efferent anode set 44 typically comprises a plurality of virtual-cathode-inhibiting anodes 44a, one or more of which is activated at any time based on the expected magnitude and location of the virtual cathode effect.

Likewise, afferent anode set 45 typically comprises a plurality of anodes 45, typically two anodes 45a and 45b, in order to minimize the virtual cathode effect in the direction of the brain. In certain electrode configurations, cathode 46 comprises a plurality of cathodes in order to minimize the "virtual anode effect," which is analogous to the virtual cathode effect.

FIG. 2C is a simplified perspective illustration of electrode device 40 (FIG. 2A), in accordance with an embodiment of the present invention. When applied to vagus nerve 36, electrode device 40 typically encompasses the nerve. As described, control unit 20 typically drives electrode device 40 to (i) apply signals to vagus nerve 36 in order to induce the propagation of efferent action potentials towards heart 30, and (ii) suppress artificially-induced afferent action potentials towards brain 34. The electrodes typically comprise ring electrodes adapted to apply a generally uniform current around the circumference of the nerve, as best shown in FIG. 2C.

Alternatively, ordinary, non-cuff electrodes are used, such as when the electrodes are placed on the epicardial fat pads instead of on the vagus nerve.

FIG. 3 is a conceptual illustration of the application of current to vagus nerve 36 in order to achieve smaller-to-larger diameter fiber recruitment, in accordance with an embodiment of the present invention. When inducing efferent action potentials towards heart 30, control unit 20 drives electrode device 40 to selectively recruit nerve fibers beginning with smaller-diameter fibers and to progressively recruit larger-diameter fibers as the desired stimulation level increases. This smaller-to-larger diameter recruitment order mimics the body's natural order of recruitment.

Typically, in order to achieve this recruitment order, the control unit stimulates myelinated fibers essentially of all diameters using cathodic current from cathode 46, while simultaneously inhibiting fibers in a larger-to-smaller diameter order using efferent anodal current from efferent anode set 44. For example, FIG. 3 illustrates the recruitment of a single, smallest nerve fiber 56, without the recruitment of any larger fibers 50, 52 and 54. The depolarizations generated by cathode 46 stimulate all of the nerve fibers shown, producing action potentials in both directions along all the nerve fibers. Efferent anode set 44 generates a hyperpolarization effect sufficiently strong to block only the three largest nerve fibers 50, 52 and 54, but not fiber 56. This blocking order of larger-to-smaller diameter fibers is achieved because larger nerve fibers are inhibited by weaker anodal currents than are smaller nerve fibers. Stronger anodal currents inhibit progressively smaller nerve fibers. When the action potentials induced by cathode 46 in larger fibers 50, 52 and 54 reach the hyperpolarized region in the larger fibers adjacent to efferent anode set 44, these action potentials are blocked. On the other hand, the action potentials induced by cathode 46 in smallest fiber 56 are not blocked, and continue traveling unimpeded toward heart 30. Anode pole 44a is shown generating less current than anode pole 44b in order to minimize the virtual cathode effect in the direction of the heart, as described above.

When desired, in order to increase the parasympathetic stimulation delivered to the heart, the number of fibers not blocked is progressively increased by decreasing the amplitude of the current applied by efferent anode set 44. The action potentials induced by cathode 46 in the fibers now not blocked travel unimpeded towards the heart. As a result, the parasympathetic stimulation delivered to the heart is progressively increased in a smaller-to-larger diameter fiber order, mimicking the body's natural method of increasing stimulation. Alternatively or additionally, in order to increase the number of fibers stimulated, while simultaneously decreasing the average diameter of fibers stimulated, the amplitudes of the currents applied by cathode 46 and efferent anode set 44 are both increased (thereby increasing both the number of fibers stimulated and blocked). In addition, for any given number of fibers stimulated (and not blocked), the amount of stimulation delivered to the heart can be increased by increasing the PPT, frequency, and/or pulse width of the current applied to vagus nerve 36.

In order to suppress artificially-induced afferent action potentials from traveling towards the brain in response to the cathodic stimulation, control unit 20 typically drives electrode device 40 to inhibit fibers 50, 52, 54 and 56 using afferent anodal current from afferent anode set 45. When the afferent-directed action potentials induced by cathode 46 in all of the fibers reach the hyperpolarized region in all of the fibers adjacent to afferent anode set 45, the action potentials are blocked. Blocking these afferent action potentials generally minimizes any unintended side effects, such as undesired or counterproductive feedback to the brain, that might be caused by these action potentials. Anode 45b is shown generating less current than anode 45a in order to minimize the virtual cathode effect in the direction of the brain, as described above.

In an embodiment of the present invention, the amplitude of the cathodic current applied in the vicinity of the vagus nerve is between about 2 milliamps and about 10 milliamps. Such a current is typically used in embodiments that employ techniques for achieving generally uniform stimulation of the vagus nerve, i.e., stimulation in which the stimulation applied to fibers on or near the surface of the vagus nerve is generally no more than about 400% greater than stimulation applied to fibers situated more deeply in the nerve. This corresponds to stimulation in which the value of the activation function at fibers on or near the surface of the vagus nerve is generally no more than about four times greater than the value of the activation function at fibers situated more deeply in the nerve. For example, as described hereinabove with reference to FIG. 2A, the electrodes may be recessed so as not to come in direct contact with vagus nerve 24, in order to achieve generally uniform values of the activation function. Typically, but not necessarily, embodiments using approximately 5 mA of cathodic current have the various electrodes disposed approximately 0.5 to 2.5 mm from the axis of the vagus nerve. Alternatively, larger cathodic currents (e.g., 10-30 mA) are used in combination with electrode distances from the axis of the vagus nerve of greater than 2.5 mm (e.g., 2.5-4.0 mm), so as to achieve an even greater level of uniformity of stimulation of fibers in the vagus nerve.

In an embodiment of the present invention, the cathodic current is applied by cathode 46 with an amplitude sufficient to induce action potentials in large- and medium-diameter fibers 50, 52, and 54 (e.g., A- and B-fibers), but insufficient to induce action potentials in small-diameter fibers 56 (e.g., C-fibers). Simultaneously, an anodal current is applied by anode 44b in order to inhibit action potentials induced by the cathodic current in the large-diameter fibers (e.g., A-fibers). This combination of cathodic and anodal current generally results in the stimulation of medium-diameter fibers (e.g., B-fibers) only. At the same time, a portion of the afferent action potentials induced by the cathodic current are blocked by anode 45a, as described above. Alternatively, the afferent anodal current is configured to not fully block afferent action potentials, or is simply not applied. In these cases, artificial afferent action potentials are nevertheless generally not generated in C-fibers, because the applied cathodic current is not strong enough to generate action potentials in these fibers.

These techniques for efferent stimulation of only B-fibers are typically used in combination with techniques described hereinabove for achieving generally uniform stimulation of the vagus nerve. Such generally uniform stimulation enables the use of a cathodic current sufficiently weak to avoid stimulation of C-fibers near the surface of the nerve, while still sufficiently strong to stimulate B-fibers, including B-fibers situated more deeply in the nerve, i.e., near the center of the nerve. For some applications, when employing such techniques for achieving generally uniform stimulation of the vagus nerve, the amplitude of the cathodic current applied by cathode 46 may be between about 3 and about 10 milliamps, and the amplitude of the anodal current applied by anode 44b may be between about 1 and about 7 milliamps. (Current applied at a different site and/or a different time is used to achieve a net current injection of zero.)

In an embodiment of the present invention, stimulation of the vagus nerve is applied responsive to one or more sensed parameters. Control unit 20 is typically configured to commence or halt stimulation, or to vary the amount and/or timing of stimulation in order to achieve a desired target heart rate, typically based on configuration values and on parameters including one or more of the following:

- Heart rate—the control unit can be configured to drive electrode device 26 to stimulate the vagus nerve only when the heart rate exceeds a certain value.
- ECG readings—the control unit can be configured to drive electrode device 26 to stimulate the vagus nerve based on certain ECG readings, such as readings indicative of designated forms of arrhythmia. Additionally, ECG readings are typically used for achieving a desire heart rate, as described below with reference to FIG. 7.
- Blood pressure—the control unit can be configured to regulate the current applied by electrode device 26 to the vagus nerve when blood pressure exceeds a certain threshold or falls below a certain threshold.
- Indicators of decreased cardiac contractility—these indicators include left ventricular pressure (LVP). When LVP and/or d(LVP)/dt exceeds a certain threshold or falls below a certain threshold, control unit 20 can drive electrode device 26 to regulate the current applied by electrode device 26 to the vagus nerve.
- Motion of the subject—the control unit can be configured to interpret motion of the subject as an indicator of increased exertion by the subject, and appropriately reduce parasympathetic stimulation of the heart in order to allow the heart to naturally increase its rate.
- Heart rate variability—the control unit can be configured to drive electrode device 26 to stimulate the vagus nerve based on heart rate variability, which is typically calculated based on certain ECG readings.
- Norepinephrine concentration—the control unit can be configured to drive electrode device 26 to stimulate the vagus nerve based on norepinephrine concentration.
- Cardiac output—the control unit can be configured to drive electrode device 26 to stimulate the vagus nerve based on cardiac output, which is typically determined using impedance cardiography.
- Baroreflex sensitivity—the control unit can be configured to drive electrode device 26 to stimulate the vagus nerve based on baroreflex sensitivity.
- LVEDP—the control unit can be configured to drive electrode device 26 to stimulate the vagus nerve based on LVEDP, which is typically determined using a pressure gauge, as described hereinabove with reference to FIG. 1.

The parameters and behaviors included in this list are for illustrative purposes only, and other possible parameters and/or behaviors will readily present themselves to those skilled in the art, having read the disclosure of the present patent application.

In an embodiment of the present invention, control unit 20 is configured to drive electrode device 26 to stimulate the vagus nerve so as to reduce the heart rate of the subject towards a target heart rate. The target heart rate is typically (a) programmable or configurable, (b) determined responsive to one or more sensed physiological values, such as those described hereinabove (e.g., motion, blood pressure, etc.), and/or (c) determined responsive to a time of day or circadian cycle of the subject. Parameters of stimulation are varied in real time in order to vary the heart-rate-lowering effects of the stimulation. For example, such parameters may include the amplitude of the applied current. Alternatively or additionally, in an embodiment of the present invention, the stimulation is applied in bursts (i.e., series of pulses), which are synchronized or are not synchronized with the cardiac cycle of the subject, such as described hereinbelow with reference to FIG. 7. Parameters of such bursts typically include, but are not limited to:

- Timing of the stimulation within the cardiac cycle. Delivery of each of the bursts typically begins after a fixed or variable delay following an ECG feature, such as each R- or P-wave. For some applications, the delay is between about 20 ms and about 700 ms after the R-wave (e.g., about 100 ms after the R-wave), or between about 100 and about 500 ms after the P-wave.
- Pulse duration (width). Longer pulse durations typically result in a greater heart-rate-lowering effect. For some applications, the pulse duration is between about 0.1 and about 4 ms, such as between about 100 microseconds and about 2.5 ms, e.g., about 1 ms.
- Pulse repetition interval within each burst. Maintaining a pulse repetition interval (the time from the initiation of a pulse to the initiation of the following pulse within the same burst) greater than about 3 ms generally results in maximal stimulation effectiveness for multiple pulses within a burst. For some applications, the pulse repetition interval is between about 1 and about 20 ms, such as between about 3 and about 10 ms, e.g., about 6 ms.
- Pulses per trigger (PPT). A greater PPT (the number of pulses in each burst after a trigger such as an R-wave) typically results in a greater heart-rate-lowering effect. For some applications, PPT is between about 0 and about 20 pulses, such as between about 1 and about 10 pulses, e.g., 3 pulses. For some applications, PPT is varied while pulse repetition interval is kept constant.
- Amplitude. A greater amplitude of the signal applied typically results in a greater heart-rate-lowering effect. The amplitude is typically less than about 20 milliamps, e.g., between about 0.1 and about 9 milliamps, e.g., about 2.5 milliamps. For some applications, the amplitude is between about 2 and about 6 milliamps.
- Duty cycle (number of bursts per heart beat). Application of stimulation every heartbeat (i.e., with a duty cycle of 1) typically results in a greater heart-rate-lowering effect. For less heart rate reduction, stimulation is applied less frequently than every heartbeat (e.g., duty cycle=60%-90%), or only once every several heartbeats (e.g., duty cycle=5%-40%).
- Choice of vagus nerve. Stimulation of the right vagus nerve typically results in greater heart rate reduction than stimulation of the left vagus nerve.
- "On"/"off" ratio and timing. For some applications, the device operates intermittently, alternating between "on" and "off" states, the length of each state typically being between 0 and about 1 day, such as between 0 and about 300 seconds (with a 0-length "off" state equivalent to always "on"). No stimulation is applied during the "off" state. Greater heart rate reduction is typically achieved if the device is "on" a greater portion of the time.

For some applications, values of one or more of the parameters are determined in real time, using feedback, i.e., responsive to one or more inputs, such as sensed physiological values. For example, the intermittency ("on"/"off") parameter may be determined in real time using such feedback. The inputs used for such feedback typically include one or more of the following: (a) motion or activity of the subject (e.g., detected using an accelerometer), (b) the average heart rate of the subject, (c) the average heart rate of the subject when the device is in "off" mode, (d) the average heart rate of the subject when the device is in "on" mode, and/or (e) the time of day. The average heart rate is typically calculated over a period of at least about 10 seconds. For some applications, the average heart rate during an "on" or "off" period is calculated over the entire "on" or "off" period. For example, the device may operate in continuous "on" mode when the subject is exercising and therefore has a high heart rate, and the device may alternate between "on" and "off" when the subject is at rest. As a result, the heart-rate-lowering effect is concentrated during periods of high heart rate, and the nerve is allowed to rest when the heart rate is generally naturally lower. For some applications, the device determines the ratio of "on" to "off" durations, the duration of the "on" periods, and/or the durations of the "off" periods using feedback. Optionally, the device determines the "on"/"off" parameter in real time using the integral feedback techniques described hereinbelow, and/or other feedback techniques described hereinbelow, mutatis mutandis.

For some applications, heart rate regulation is achieved by setting two or more parameters in combination. For example, if it is desired to apply 5.2 pulses of stimulation, the control unit may apply 5 pulses of 1 ms duration each, followed by a single pulse of 0.2 ms duration. For other applications, the control unit switches between two values of PPT, so that the desired PPT is achieved by averaging the applied PPTs. For example, a sequence of PPTs may be 5, 5, 5, 5, 6, 5, 5, 5, 5, 6, . . . , in order to achieve an effective PPT of 5.2.

Figure 4:
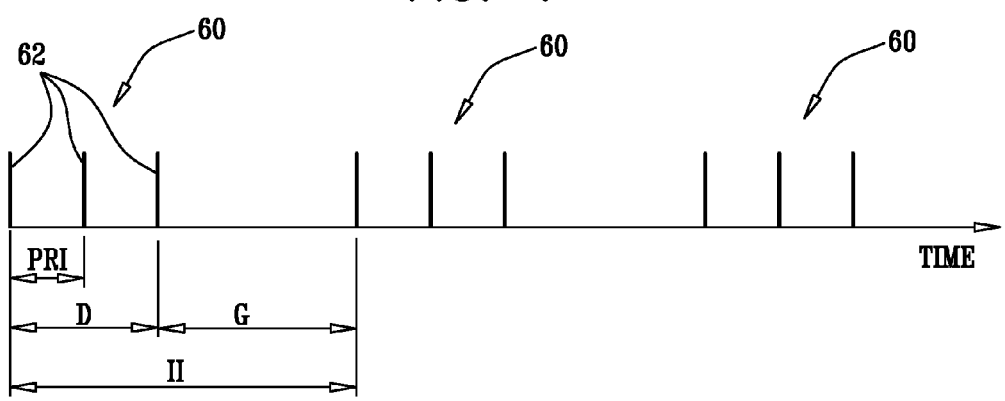
FIG. 4 is a schematic illustration of a series of bursts, in accordance with an embodiment of the present invention.

Reference is made to FIG. 4, which is a schematic illustration of a series of bursts 60, in accordance with an embodiment of the present invention. Control unit 20 is configured to drive electrode device 26 to apply stimulation in the series of bursts 60, at least one of which bursts includes a plurality of pulses 62, such as at least three pulses 62. Control unit 20 configures:

(a) a pulse repetition interval (PRI) within each of multi-pulse bursts 60 (i.e., the time from the initiation of a pulse to the initiation of the following pulse within the same burst) to be on average at least 20 ms, such as at least 30 ms, e.g., at least 50 ms or at least 75 ms, and (b) an interburst interval (II) (i.e., the time from the initiation of a burst to the initiation of the following burst) to be at least a multiple M times the burst duration D. Multiple M is typically at least 1.5 times the burst duration D, such as at least 2 times the burst duration, e.g., at least 3 or 4 times the burst duration. (Burst duration D is the time from the initiation of the first pulse within a burst to the conclusion of the last pulse within the burst.)

In other words, burst duration D is less than a percentage P of interburst interval II, such as less than 75%, e.g., less than 67%, 50%, or 33% of the interval. For some applications, the PRI varies within a given burst, in which case the control unit sets the PRI to be on average at least 20 ms, such as at least 30 ms, e.g., at least 50 ms or at least 75 ms. For other applications, the PRI does not vary within a given burst (it being understood that for these applications, the "average PRI" and the PRI "on average," including as used in the claims, is equivalent to the PRI; in other words, the terms "average PRI" and the PRI "on average" include within their scope both (a) embodiments with a constant PRI within a given burst, and (b) embodiments with a PRI that varies within a given burst).

Typically, each burst 60 includes between two and 14 pulses 62, e.g., between two and six pulses, and the pulse duration (or average pulse duration) is between about 0.1 and about 4 ms, such as between about 100 microseconds and about 2.5 ms, e.g., about 1 ms. Typically, control unit 20 sets the interburst interval II to be less than 10 seconds. For some applications, control unit 20 is configured to set the interburst interval II to be between 400 ms and 1500 ms, such as between 750 ms and 1500 ms. Typically, control unit 20 sets an interburst gap G between a conclusion of each burst 60 and an initiation of the following burst 60 to have a duration greater than the PRI. For some applications, the duration of the interburst gap G is at least 1.5 times the PRI, such as at least 2 times the PRI, at least 3 times the PRI, or at least 4 times the PRI.

Although the control unit typically withholds applying current during the periods between bursts and between pulses, it is to be understood that the scope of the present invention includes applying a low level of current during such periods, such as less than 50% of the current applied during the "on" periods, e.g., less than 20% or less than 5%. Such a low level of current is hypothesized to have a different, significantly lower, or a minimal physiological effect on the subject. For some applications, control unit 20 is configured to apply an interburst current during at least a portion of interburst gap G, and to set the interburst current on average to be less than 50% (e.g., less than 20%) of the current applied on average during the burst immediately preceding the gap. For some applications, control unit 20 is configured to apply an interpulse current to the site during at least a portion of the time that the pulses of bursts 60 are not being applied, and to set the interpulse current on average to be less than 50% (e.g., less than 20%) of the current applied on average during bursts 60.

For some applications, the control unit is configured to synchronize the bursts with a feature of the cardiac cycle of the subject. For example, each of the bursts may commence after a delay after a detected R-wave, P-wave, or other feature of an ECG. For these applications, one burst is typically applied per heart beat, so that the interburst interval II equals the R-R interval, or a sum of one or more sequential R-R intervals of the subject. Alternatively, for some applications, the control unit is configured to synchronize the bursts with other physiological activity of the subject, such as respiration, muscle contractions, or spontaneous nerve activity.

In an embodiment of the present invention, the control unit sets the PRI to at least 75% of a maximum possible PRI for a given interburst interval II (such as the R-R interval of the subject), desired percentage P, and desired PPT. For some applications, the following equation is used to determine the maximum possible PRI:

$$PRI = II * P / (PPT - 1) \qquad \text{(Equation 1)}$$

For example, if the II is 900 ms, percentage P is 33.3%, and the desired PPT is 4 pulses, the maximum possible PRI would be 900 ms*33.3%/(4−1)=100 ms, and the control unit would set the actual PRI to be at least 75 ms. For some applications, control unit 20 uses this equation to determine the PRI, such as in real time or periodically, while for other applications this equation is used to produce a look-up table which is stored in the control unit. For still other applications, this equation is used to configure the control unit. For some applications, multiple M is a constant, which is stored in control unit 20, while for other applications, control unit 20 adjusts M during operation, such as responsively to one or more sensed physiological values, or based on the time of day, for example. It is noted that Equation 1 assumes that the pulse width of the pulses does not contribute meaningfully to burst duration D. Modifications to Equation 1 to accommodate longer pulse widths will be evident to those skilled in the art.

For some applications, when using Equation 1, a maximum value is set for the PRI, such as between 175 and 225, e.g., about 200, and the PRI is not allowed to exceed this maximum value regardless of the result of Equation 1.

In an experiment conducted on three human subjects, the inventors found that increasing the PRI of the applied stimulation reduced sensations of acute pain experienced by the subjects. In each of the subjects, two stimulation regimens were a applied: (a) stimulation with bursts having a PPT of 3 and a PRI of 6 ms, synchronized with the cardiac cycle, and (b) stimulation with single-pulse (i.e., a PPT of 1) bursts at three times the heart rate, but not synchronized with the cardiac cycle. Regimen (b) had an effective PRI of about 300 ms. The overall number of pulses per minute was thus three times the heart rate in both regimens. Stimulation with the extended PRI of regimen (b) resulted in acute pain that was markedly attenuated compared to stimulation with the shorter PRI of regimen (a). (However, it was observed that stimulation with regimen (b) quickly caused secondary neuropathic pain projecting along the mandible, as described below with reference to FIG. 6. The inventors attribute the occurrence of such secondary pain to the shorter non-stimulation periods between pulses of regimen (b) compared to regimen (a).)

Figure 5:
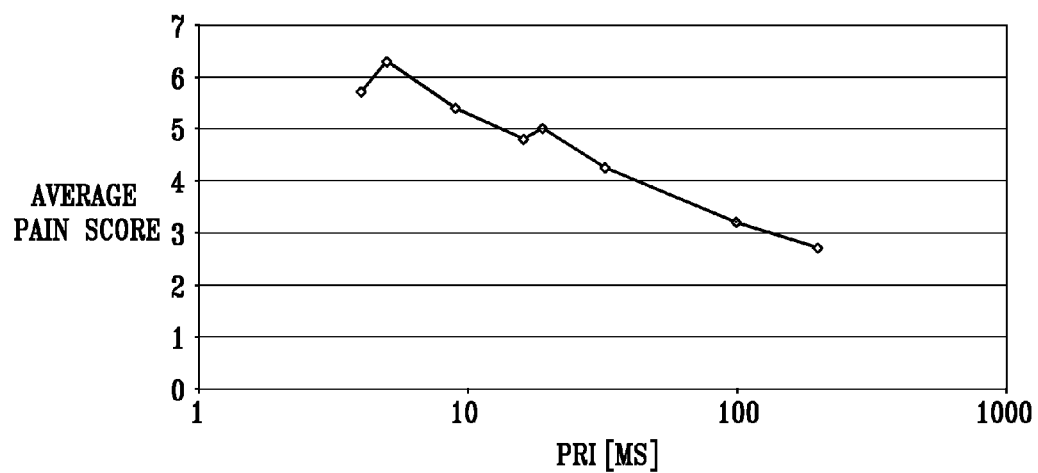
FIG. 5 is a graph showing experimental results obtained in an experiment performed on human subjects, in accordance with an embodiment of the present invention.

FIG. 5 is a graph showing experimental results obtained in an experiment performed on human subjects, in accordance with an embodiment of the present invention. The digital nerves of five healthy volunteers were stimulated using an external stimulator in several stimulation sessions. During each stimulation session, a single burst was applied, having a PPT of 4, an amplitude of 1 to 5 mA, and a pulse width of 1 ms. Each of the sessions was randomly assigned a PRI, without the knowledge of the subjects, and the subjects scored the pain associated with each session on a scale of 1 to 10, with higher values representing greater perceived acute neuropathic pain. The graph reflects the averaged pain scores for different PRIs across all five subjects. As can be seen in the graph, greater PRIs were strongly correlated with reduced acute pain scores.

In an embodiment, these extended PRI techniques are applied to stimulation of nerves other than the vagus nerve.

Figure 6:
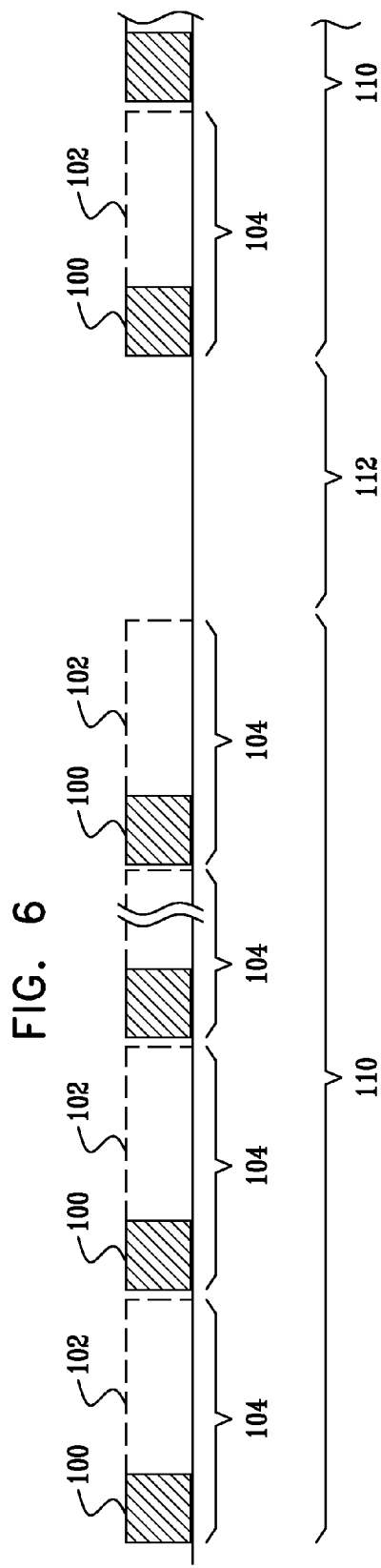
FIG. 6 is a schematic illustration of a stimulation regimen, in accordance with an embodiment of the present invention.

Reference is made to FIG. 6, which is a schematic illustration of a stimulation regimen, in accordance with an embodiment of the present invention. Control unit 20 is configured to apply the stimulation during "on" periods 100 alternating with "off" periods 102, during which no stimulation is applied (each set of a single "on" period followed by a single "off" period is referred to hereinbelow as a "cycle" 104). Typically, each of "on" periods 100 has an "on" duration equal to at least 1 second (e.g., between 1 and 10 seconds), and each of "off" periods 102 has an "off" duration equal to at least 50% of the "on" duration, e.g., at least 100% or 200% of the "on" duration. Control unit 20 is further configured to apply such intermittent stimulation during stimulation periods 110 alternating with rest periods 112, during which no stimulation is applied. Each of rest periods 102 typically has a duration equal to at least the duration of one cycle 104, e.g., between one and 50 cycles, such as between two and four cycles, and each of stimulation periods 110 typically has a duration equal to at least 5 times the duration of one of rest periods 112, such as at least 10 times, e.g., at least 15 times. For example, each of stimulation periods 110 may have a duration of at least 30 cycles, e.g., at least 60 cycles or at least 120 cycles, and no greater than 2400 cycles, e.g., no greater than 1200 cycles. Alternatively, the duration of the stimulation and rest periods are expressed in units of time, and each of the rest periods has a duration of at least 30 seconds, e.g., such as at least one minute, at least two minutes, at least five minutes, or at least 25 minutes, and each of the stimulation periods has a duration of at least 10 minutes, e.g., at least 30 minutes, such as at least one hour, and less than 12 hours, e.g., less than six hours, such as less than two hours.

For some applications, low stimulation periods are used in place of "off" periods 102. During these low stimulation periods, the control unit sets the average current applied to be less than 50% of the average current applied during the "on" periods, such as less than 20% or less than 5%. Similarly, for some applications, the control unit is configured to apply a low level of current during the rest periods, rather than no current. For example, the control unit may set the average current applied during the rest periods to be less than 50% of the average current applied during the "on" periods, such as less than 20% or less than 5%. As used in the present application, including in the claims, the "average current" or "current applied on average" during a given period means the total charge applied during the period (which equals the integral of the current over the period, and may be measured, for example, in coulombs) divided by the duration of the period, such that the average current may be expressed in mA, for example.

In human experiments conducted by the inventors, it was observed in three subjects that application of continuous intermittent stimulation (i.e., without providing the rest periods described above) for long periods of time (e.g., several hours or several days) caused secondary neuropathic pain projecting along the mandible. Such pain was also observed to commence within several minutes of application of constant stimulation (i.e., non-intermittent stimulation). Providing a rest period of as brief as 30 seconds caused the immediate elimination of this pain. Such pain did not immediately return upon resumption of intermittent stimulation, but did recur after several hours of such stimulation. Providing a longer rest period of several minutes duration once every several hours eliminated this neuropathic pain and prevented its recurrence.

For some applications, these rest period stimulation techniques are combined with the extended PRI techniques described hereinabove with reference to FIG. 4.

In an embodiment, these rest period stimulation techniques are applied to stimulation of nerves other than the vagus nerve.

In an embodiment of the present invention, control unit 20 is configured to apply electrical stimulation to a site, such as the vagus nerve, or one of the other sites described hereinabove, for at least three hours, which at least three hours includes a period having a duration of three hours, which period is divided into a number of equal-duration sub-periods such that each of the sub-periods has a sub-period duration equal to three hours divided by the number of sub-periods, the number between 5 and 10. The control unit configures the stimulation to cause, during at least 20% of each of the sub-periods, an average reduction of at least 5% in a heart rate of the subject compared to a baseline heart rate of the subject. The control unit additionally configures the stimulation to not cause secondary neuropathic pain, such as, by way of non-limiting example, by using one or more techniques described herein. Typically, the control unit additionally configures the stimulation to not cause local pain in a vicinity of the site. For some applications, the control unit configures the stimulation to cause the average reduction during at least 40% of each of the sub-periods. For some applications, the number of sub-periods equals 6 or 9, such that the sub-period duration equals 30 minutes or 20 minutes, respectively.

In an embodiment of the present invention, control unit 20 is configured to apply electrical stimulation to a site, such as a site of the vagus nerve, or another of the sites described hereinabove, for at least three hours, which at least three hours includes a period having a duration of three hours. The control unit configures the stimulation to include at least 3000 pulses during the period, the pulses having on average a pulse duration of at least 0.5 ms (e.g., at least 9 ms), and configures the stimulation to cause, on average during the pulses, at least 3 mA to enter tissue of the vagus nerve. (Depending on the configuration of the electrode device, a portion of the current applied by the device typically does not enter the vagus nerve; the at least 3 mA does not include such current that does not actually enter the vagus nerve.) The control unit additionally configures the stimulation to not cause secondary neuropathic pain, such as, by way of non-limiting example, by using one or more techniques described herein. Typically, the control unit additionally configures the stimulation to not cause local pain in a vicinity of the site. For some applications, the control unit configures the stimulation to cause, on average during the pulses, at least 4 mA to enter the tissue of the vagus nerve.

For some applications, the control unit configures the stimulation to include at least 5000 pulses during the period. For example, if the stimulation were to be applied in a single pulse per second over the three-hour period with a duty cycle of 50% (i.e., the total duration of the "on" periods over the three-hour period equals the total duration of the "off" periods over the three-hour period), a total of 5,400 pulses would be applied (=50%*3 hr*3600 pulses/hr). Without the use of at least one pain reduction technique, such stimulation would generally cause secondary neuropathic pain by the end of the three-hour period. Using techniques described herein, such as, for example, rest periods, a relatively-small portion of the pulses (e.g., up to about 7.5% of the pulses, in this case about 400 of the pulses) are not applied, thereby preventing such secondary neuropathic pain.

In an embodiment of the present invention, control unit 20 is configured to apply the bursts using short "on" periods and, optionally, short "off" periods. Each of the short "on" periods typically has a duration of less than about 10 seconds, e.g., less than about 5 seconds. When short "off" periods are used, each of the "off" periods typically has a duration of between about 5 and about 10 seconds. For example, the "on" periods may have a duration of about 3 seconds, and the "off" periods may have a duration of about 6 seconds. (Stimulation having the configuration described in this paragraph is referred to hereinbelow as "fast intermittent stimulation.") The use of such short periods generally allows stimulation of any given strength (e.g., as measured by amplitude of the signal, or by PPT of the signal) to be applied as effectively as when using longer "on"/"off" periods, but with fewer potential side effects. In addition, the use of such short "on" periods generally allows side-effect-free application of stimulation at a strength that might increase the risk of side effects if applied for longer "on" periods. It is believed by the inventors that the use of such short periods generally reduces side effects by preventing build-up of sympathetic tone. In general, the parasympathetic reaction to vagal stimulation occurs more quickly than the sympathetic reaction to vagal stimulation. The short "on" periods are sufficiently long to stimulate a desired meaningful parasympathetic reaction, but not sufficiently long to stimulate an undesired, potentially side-effect-causing sympathetic reaction.

For some applications, a desired number of pulses per time period or per heart beat is delivered more effectively and/or with a reduced risk of side effects, by using short "on" periods. For example, assume that it is desired to apply one pulse per trigger. Without the use of short "on" periods, one pulse per trigger could be achieved by applying one PPT constantly. Using short "on" periods, one pulse per trigger could instead be achieved by applying 3 PPT for 3 heart beats (the "on" period), followed by an "off" period of 6 heart beats without stimulation. In both cases, in any given 9-heart-beat period, the same number of pulses (9) are applied. However, the use of short "on" periods generally increases the effectiveness and reduces the potential side effects of the stimulations.

In an embodiment of the present invention, control unit 20 is configured to apply vagal stimulation intermittently using "on"/"off" periods, the durations of which are expressed in heart beats, rather than in units of time. In other words, the control unit alternatingly applies the stimulation for a first number of heart beats, and withholds applying the stimulation for a second number of heart beats. For example, the control unit may alternatingly apply the stimulation for between about 1 and about 30 heart beats, and withhold applying the stimulation for between about 5 and about 300 heart beats. Expressing the duration of the "on"/"off" periods in heart beats results in a constant duty cycle (expressed as "on"/ ("on"+"off")), while expressing the duration in units of time results in a variable duty cycle. In addition, expressing the duration of the "on"/"off" periods in heart beats results in the duration of the "on" and "off" periods varying based on the heart rate (at higher heart rates, the "on" and "off" periods are shorter). Furthermore, expressing the duration of the "on"/ "off" periods in heart beats tends to synchronize the stimulation with breathing, which is usually more rapid when the heart rate increases, such as during exercise.

For one particular application, the control unit alternatingly applies the stimulation for exactly one heart beat, and withholds applying the stimulation for exactly one heart beat, i.e., the control unit applies the stimulation every other heart beat. Expressing the duration of "on"/"off" periods in heart beats typically allows precise control of the amount of stimulation applied and the physiological parameter that is being modified, e.g., heart rate.

In an embodiment of the present invention, control unit 20 is configured to apply vagal stimulation intermittently using "on"/"off" periods, the duration of one of which type of periods is expressed in heart beats, and of the other is expressed in units of time. For example, the duration of the "on" periods may be expressed in heart beats (e.g., 2 heart beats), and the duration of the "off" periods may be expressed in seconds (e.g., 2 seconds). In other words, in this example, the control unit alternatingly applies the stimulation for a number of heart beats, and withholds applying the stimulation for a number of seconds. For example, the control unit may alternatingly apply the stimulation for between about 1 and about 100 heart beats, and withhold applying the stimulation for between about 1 and about 100 seconds. Expressing the duration of the "on"/"off" periods in this manner results in an automatic reduction of the duty cycle as the heart rate increases, because, at higher heart rates, more heart beats occur during the "off" periods. As a result, stimulation is automatically reduced at higher rates, which may allow for increased activity and improved quality of life.

In an embodiment of the present invention, control unit 20 is configured to operate intermittently. Typically, upon each resumption of operation, control unit 20 sets the stimulation parameters to those in effect immediately prior to the most recent cessation of operation. For some applications, such parameters applied upon resumption of operation are maintained without adjustment for a certain number of heartbeats (e.g., between about one and about ten), in order to allow the heart rate to stabilize after resumption of operation.

For some applications, control unit 20 is configured to operate intermittently with gradual changes in stimulation. For example, the control unit may operate according to the following "on"/"off" pattern: (a) "off" mode for 30 minutes, (b) a two-minute "on" period characterized by a gradual increase in stimulation so as to achieve a target heart rate, (c) a six-minute "on" period of feedback-controlled stimulation to maintain the target heart rate, and (d) a two-minute "on" period characterized by a gradual decrease in stimulation to return the heart rate to baseline. The control unit then repeats the cycle, beginning with another 30-minute "off" period.

In an embodiment of the present invention, the heart rate regulation algorithm utilizes sensed physiological parameters for feedback. For some applications, the feedback is updated periodically by inputting the current heart rate. For some applications, such updating occurs at equally-spaced intervals. Alternatively, the feedback is updated by inputting the current heart rate upon each detection of a feature of the ECG, such as an R-wave. In order to convert non-fixed R-R intervals into a form similar to canonical fixed intervals, the algorithm adds the square of each R-R interval, thus taking into account the non-uniformity of the update interval, e.g., in order to properly analyze feedback stability using standard tools and methods developed for canonical feedback.

In an embodiment of the present invention, the amplitude of the applied stimulation current is calibrated by fixing a number of pulses in the series of pulses (per cardiac cycle), and then increasing the applied current until a desired predetermined heart rate reduction is achieved. Alternatively, the current is calibrated by fixing the number of pulses per series of pulses, and then increasing the current to achieve a substantial reduction in heart rate, e.g., 40%.

In embodiments of the present invention in which vagal stimulation system 18 comprises implanted device 25 for monitoring and correcting the heart rate, control unit 20 typically uses measured parameters received from device 25 as additional inputs for determining the level and/or type of stimulation to apply. Control unit 20 typically coordinates its behavior with the behavior of device 25. Control unit 20 and device 25 typically share sensors 28 in order to avoid redundancy in the combined system.

Figure 7:
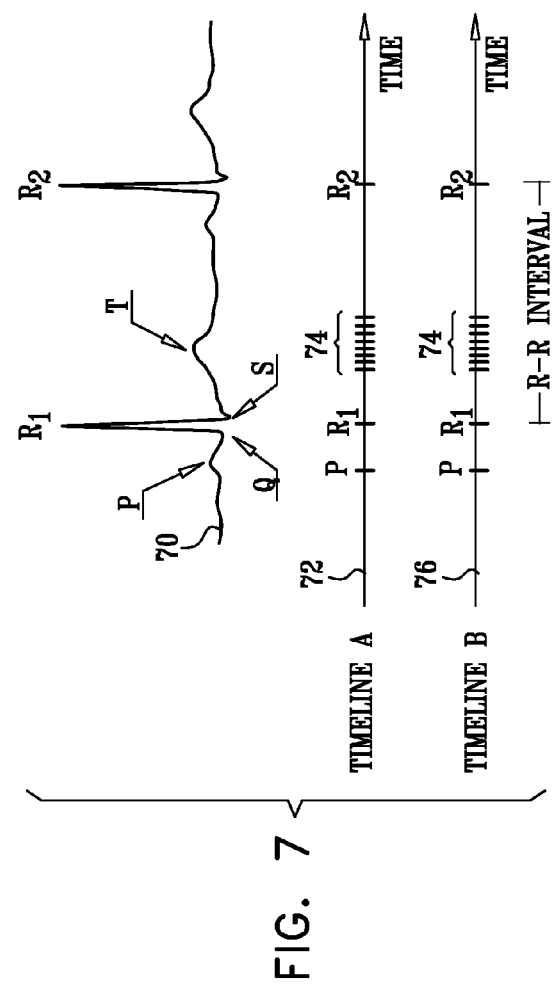
FIG. 7 is a simplified illustration of an electrocardiogram (ECG) recording and of example timelines showing the timing of the application of a series of stimulation pulses, in accordance with an embodiment of the present invention.

FIG. 7 is a simplified illustration of an ECG recording 70 and example timelines 72 and 76 showing the timing of the application of a burst of stimulation pulses 74, in accordance with an embodiment of the present invention. Stimulation is typically applied to vagus nerve 36 in a closed-loop system in order to achieve and maintain the desired target heart rate, determined as described above. Precise graded slowing of the heart beat is typically achieved by varying the number of nerve fibers stimulated, in a smaller-to-larger diameter order, and/or the intensity of vagus nerve stimulation, such as by changing the stimulation amplitude, pulse width, PPT, and/or delay. Stimulation with blocking, as described herein, is typically applied during each cardiac cycle in burst of pulses 74, typically containing between about 1 and about 20 pulses, each of about 1-3 milliseconds duration, over a period of about 1-200 milliseconds. Advantageously, such short pulse durations generally do not substantially block or interfere with the natural efferent or afferent action potentials traveling along the vagus nerve. Additionally, the number of pulses and/or their duration is sometimes varied in order to facilitate achievement of precise graded slowing of the heart beat.

In an embodiment of the present invention (e.g., when the heart rate regulation algorithm described hereinabove is not implemented), to apply the closed-loop system, the target heart rate is expressed as a ventricular R-R interval (shown as the interval between $R_1$ and $R_2$ in FIG. 7). The actual R-R interval is measured in real time and compared with the target R-R interval. The difference between the two intervals is defined as a control error. Control unit 20 calculates the change in stimulation necessary to move the actual R-R towards the target R-R, and drives electrode device 26 to apply the new calculated stimulation. Intermittently, e.g., every 1, 10, or 100 beats, measured R-R intervals or average R-R intervals are evaluated, and stimulation of the vagus nerve is modified accordingly.

In an embodiment, vagal stimulation system 18 is further configured to apply stimulation responsive to pre-set time parameters, such as intermittently, constantly, or based on the time of day.

Alternatively or additionally, one or more of the techniques of smaller-to-larger diameter fiber recruitment, selective fiber population stimulation and blocking, and varying the intensity of vagus nerve stimulation by changing the stimulation amplitude, pulse width, PPT, and/or delay, are applied in conjunction with methods and apparatus described in one or more of the patents, patent applications, articles and books cited herein.

In an embodiment of the present invention, control unit 20 operates using feedback, as described hereinabove, and is configured to target a number of pulses applied during each burst of stimulation, responsive to the feedback. Such feedback sometimes results in variations in the average number of pulses per burst. In this embodiment, control unit 20 is configured to monitor the average number of pulses per burst in a given time period. Such monitoring is performed either periodically or substantially continuously. If the average number of pulses per burst exceeds a maximum threshold value over the given time period, the control unit modifies one or more stimulation or feedback parameters, such that the average number of pulses per burst declines below the maximum threshold value. For example, the maximum threshold value may be between about 2 and about 4 pulses per burst, e.g., about 3 pulses per burst. Appropriate parameters for modification include, but are not limited to, (a) one or more of the feedback parameters, such as the target heart rate (e.g., TargetRR), and/or the feedback integral coefficient, and/or (b) one or more stimulation parameters, such as stimulation amplitude, and pulse width, and/or maximum number of pulses within a burst. Alternatively or additionally, for some applications, if the average falls below a minimum threshold value, the control unit modifies one or more stimulation or feedback parameters, such that the average number of pulses per burst increases above the minimum threshold value.

In an embodiment of the present invention, control unit 20 operates using feedback, as described hereinabove, which results in a variable number of bursts per heart beat and/or per unit time. (For example, a burst may be applied every 1-60 heart beats, or every 0.3-60 seconds, as dictated by a feedback algorithm.) Such feedback sometimes results in high- and/or low-frequency variations in the duty cycle. Control unit 20 is configured to monitor the average duty cycle in a given time period. Such monitoring is performed either periodically or substantially continuously. If the average exceeds a maximum threshold value, the control unit modifies one or more stimulation or feedback parameters, such that the average duty cycle declines below the maximum threshold value. Appropriate parameters for modification include, but are not limited to, the target heart rate (e.g., TargetRR), the feedback integral coefficient, stimulation amplitude, pulse width, and maximum number of pulses within a burst. Alternatively or additionally, for some applications, if the average falls below a minimum threshold value, the control unit modifies one or more stimulation or feedback parameters, such that the average duty cycle increases above the maximum threshold value. For some applications, control unit 20 implements the techniques of this embodiment in combination with the techniques for monitoring the average number of pulses per burst described above.

In an embodiment of the present invention, control unit 20 is configured to gradually ramp the commencement and/or termination of stimulation. In order to achieve the gradual ramp, the control unit is typically configured to gradually modify one or more stimulation parameters, such as those described hereinabove, e.g., pulse amplitude, number of pulses, PPT, pulse frequency, pulse width, "on" time, and/or "off" time. Terminating stimulation gradually, rather than suddenly, may reduce the likelihood of a rebound acceleration of heart rate that sometimes occurs upon termination of vagal stimulation. As appropriate, one or more of these parameters is varied by less than 50% of the pre-termination value per heart beat, or less than 5% per heart beat, in order to achieve the gradual ramp.

In an embodiment of the present invention, control unit 20 is configured to gradually increase the strength of stimulation according to a predetermined schedule. Such a gradual increase is typically appropriate during the first several days of use of system 18 by a new subject. Subjects sometimes experience discomfort and/or pain during their initial exposure to stimulation. Such discomfort and/or pain typically ceases after an accommodation period of several days. By gradually increasing stimulation from an initially low level, control unit 20 generally prevents such discomfort and/or pain. For example, the strength of stimulation may be increased less than 50% per hour, or less than 10% per day. The control unit is typically configured to increase the strength of stimulation by adjusting one or more stimulation parameters, such as those described hereinabove, e.g., the amplitude of the applied signal.

For some applications, system 18 is configured to allow the subject to manually control the ramp-up of stimulation, e.g., by selecting when the system proceeds to successive levels of stimulation, and/or by requesting the system to return to a previous level of stimulation.

Figure 8:
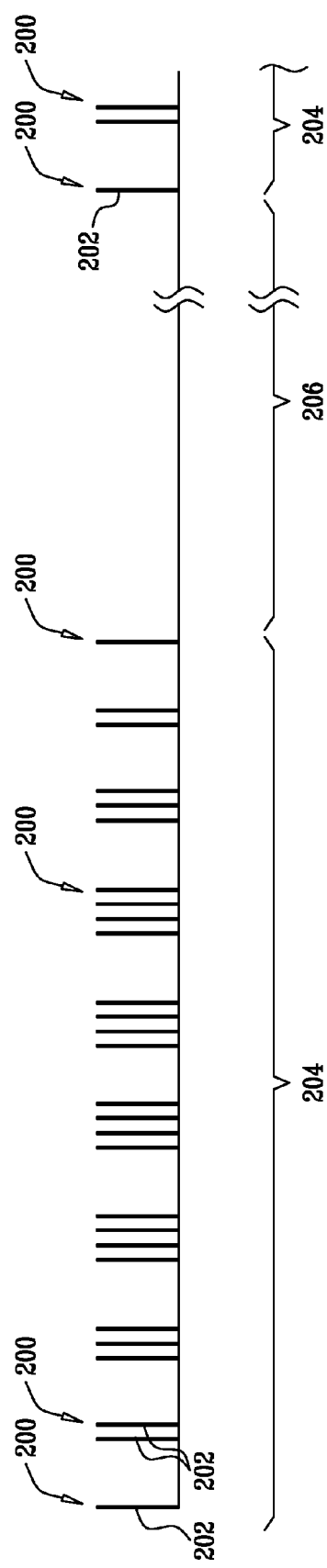
FIG. 8 is a schematic illustration of another stimulation regimen, in accordance with an embodiment of the present invention.

Reference is made to FIG. 8, which is a schematic illustration of a stimulation regimen, in accordance with an embodiment of the present invention. In this embodiment, control unit 20 is configured to apply vagal stimulation in a series of bursts 200, each of which includes one or more pulses 202 (pulses per trigger, or PPT). The control unit is configured to apply the vagal stimulation intermittently during "on" periods 204 alternating with "off" periods 206, during which no stimulation is applied. Each "on" period 204 includes at least 3 bursts 200, such as at least 10 bursts 200, and typically has a duration of between 3 and 20 seconds. At the commencement of each "on" period 204, control unit 20 ramps up the PPT of successive bursts 200, and at the conclusion of each "on" period 204, the control unit ramps down the PPT of successive bursts 200. For example, the first four bursts of an "on" period 204 may have respective PPTs of 1, 2, 3, and 3, or 1, 2, 3, and 4, and the last four bursts of an "on" period 204 may have respective PPTs of 3, 3, 2, and 1, or 4, 3, 2, and 1. Use of such ramping generally prevents or reduces sudden drops and rebounds in heart rate at the beginning and end of each "on" period, respectively. Experimental results are described hereinbelow with reference to FIG. 9 which illustrate the occurrence of such sudden drops and rebounds without the use of the ramping techniques of this embodiment.

Alternatively, rather than increase or decrease the PPT by 1 in successive bursts, control unit 20 increases or decreases the PPT more gradually, such as by 1 in less than every successive burst, e.g., the first bursts of an "on" period may have respective PPTs of 1, 1, 2, 2, 3, 3, and 4, and the last bursts of an "on" period may have respective PPTs of 4, 3, 3, 2, 2, 1, and 1. For some applications, to increase or decrease the PPT by less than 1 in successive bursts, the control unit increases or decreases the PPT by non-integer values, and achieves the non-integer portion of the increase or decrease by setting a parameter of one or more pulses other than PPT, such as pulse duration or amplitude. For example, the first bursts of an "on" period may have respective PPTs of 0.5, 1, 1.5, 2, 2.5, and 3, and the last bursts of an "on" period may have respective PPTs of 3, 2.5, 2, 1.5, 1, and 0.5. To achieve the decimal portion of these PPTs, the control unit may apply a pulse having a pulse duration equal to the decimal portion of these PPTs times the pulse duration of a full pulse. For example, if the pulse duration of a full pulse is 1 ms, a commencement ramp of 0.5, 1, and 1.5 PPT may be achieved by applying a first burst consisting of a single 0.5 ms pulse, a second burst consisting of a single 1 ms pulse, and a third burst consisting of a 1 ms pulse followed by a 0.5 ms pulse. Alternatively, to achieve the decimal portion of these PPTs, the control unit may apply a pulse having a full pulse duration but an amplitude equal to the decimal portion of these PPTs times the amplitude of a full pulse. For example, if the pulse duration and amplitude of a full pulse if 1 ms and 3 mA, respectively, a commencement ramp of 0.5, 1, and 1.5 PPT may be achieved by apply a first burst consisting of a single 1 ms pulse having an amplitude of 1.5 mA, a second burst consisting of a single 1 ms, 3 mA pulse, and a third burst consisting of a 1 ms, 3 mA followed by a 1 ms pulse having an amplitude of 1.5 mA.

For some applications, control unit 20 is configured to synchronize the bursts with a feature of the cardiac cycle of the subject. For example, each of the bursts may commence after a delay after a detected R-wave, P-wave, or other feature of an ECG. Alternatively, for some applications, the control unit is configured to synchronize the bursts with other physiological activity of the subject, such as respiration, muscle contractions, or spontaneous nerve activity. For some applications, such ramping is applied only at the commencement of each "on" period 204, or only at the conclusion of each "on" period 204, rather than during both transitional periods.

For some applications, such ramping techniques are combined with the extended PRI techniques described hereinabove with reference to FIG. 4, and/or with the rest period techniques described hereinabove with reference to FIG. 6.

Figure 9:
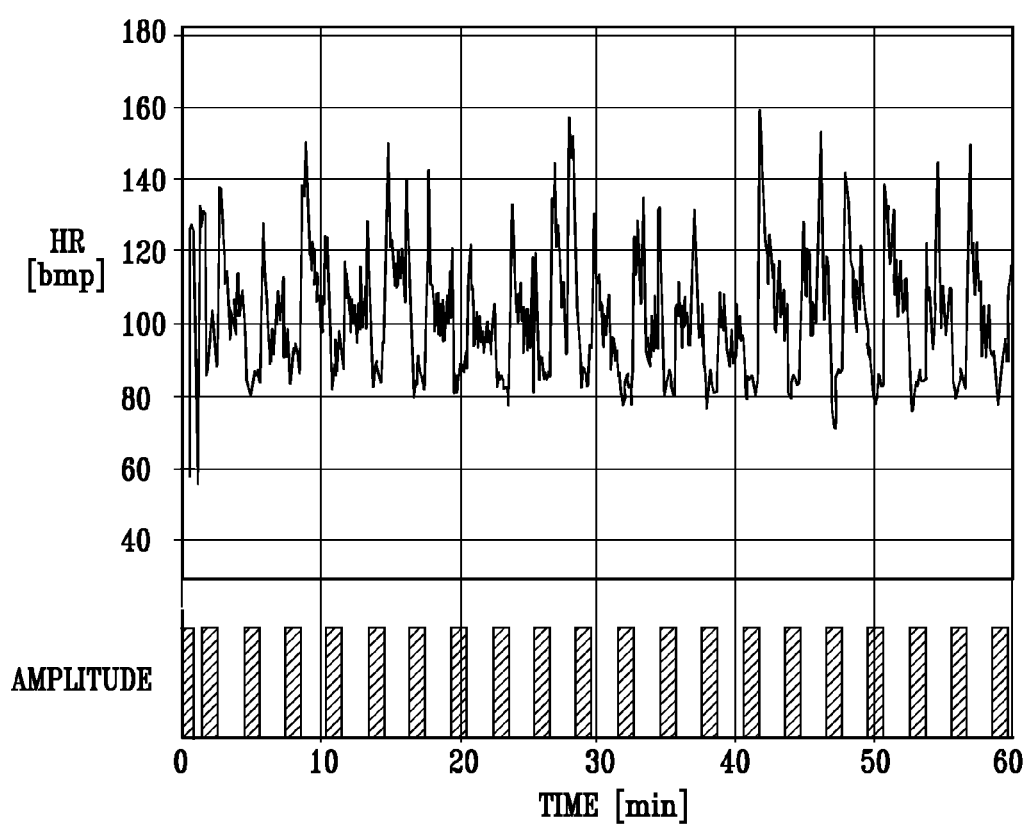
FIG. 9 is a graph showing experimental results obtained in an animal experiment, in accordance with an embodiment of the present invention.

Reference is made to FIG. 9, which is a graph showing experimental results obtained in an animal experiment, in accordance with an embodiment of the present invention. Vagal stimulation was applied to a dog in bursts of pulses during one-minute "on" periods that alternated with two-minute "off" periods. Each of the bursts had a constant PPT of 6, i.e., the stimulation was not ramped, as described hereinabove with reference to FIG. 8. As can be seen in the graph, upon initiation of each "on" period, there was a sudden and strong drop in heart rate, and immediately after the conclusion of each "on" period, there was a strong rebound in heart rate. Such abrupt drops and rebounds are particularly undesirable in patients suffering from heart disease, for whom the abrupt decreases in heart rate may cause a drop in blood pressure, and the abrupt accelerations in heart rate may cause a sensation of palpitation, or increase the risk of arrhythmia.

In an embodiment, these techniques for gradually increasing and/or decreasing the strength of stimulation are applied to stimulation of nerves other than the vagus nerve.

In an embodiment of the present invention, for applications in which control unit 20 is configured to apply vagal stimulation intermittently, as described hereinabove, the control unit begins the stimulation with an "off" period, rather than with an "on" period. As a result, a delay having the duration of an "off" period occurs prior to beginning stimulation. Alternatively or additionally, whether or not configured to apply stimulation intermittently, control unit 20 is configured to delay beginning the application of stimulation for a certain time period (e.g., a pseudo-randomly determined time period, or a predetermined fixed period of time, such as about 5 seconds) after receiving an external command to apply the stimulation. The use of these delaying techniques generally reduces a subject's anticipation of any pain or discomfort that he may associate with stimulation, and disassociates the sensations of stimulation from the physician and/or an external control device such as a wand.

For some applications, the intermittent vagal stimulation is applied with "on" periods having a duration of between about 45 and about 75 seconds each, e.g., about 1 minute each, and "off" periods having a duration of between about 90 and about 150 seconds each, e.g., about 2 minutes each. Alternatively or additionally, the intermittent vagal stimulation is applied with "off" periods having a duration of between about 1.2 and about 3.5 times greater than the "on" periods, e.g., between about 1.5 and about 2.5 times greater than the "on" periods. In order to include the plurality of different naturally-occurring heart rates, the calibration period typically includes at least several hundred "on" and "off" periods. For example, the calibration period may be about 24 hours. Alternatively, the calibration period is shorter, and includes sub-periods of rest, exercise, and recovery from exercise, in order to ensure the inclusion of the plurality of different naturally-occurring heart rates. For example, for at least part of the calibration period the subject may be subjected to an exercise test (e.g., a stress test), such as by using exercise equipment, e.g., a treadmill.

Although embodiments of the present invention are described herein, in some cases, with respect to treating specific heart conditions, it is to be understood that the scope of the present invention generally includes utilizing the techniques described herein to controllably stimulate the vagus nerve to facilitate treatments of, for example, heart failure, atrial fibrillation, and ischemic heart diseases. In particular, the techniques described herein may be performed in combination with other techniques, which are well known in the art or which are described in the references cited herein, that stimulate the vagus nerve in order to achieve a desired therapeutic end.

Although some embodiments of the present invention have been described herein with respect to applying stimulation to parasympathetic autonomic nervous tissue, it is to be understood that the scope of the present invention generally includes utilizing the techniques described herein to apply stimulation to any tissue, such as nervous tissue, muscle tissue, or sensory receptors. For example, the stimulation techniques described herein may be used to stimulate secretion by a gland, such as insulin secretion by the pancreas, or adrenalin by the adrenal gland. For these applications, the stimulation techniques described herein generally maximize the desired effect of stimulation, while generally minimizing any adverse pain, discomfort, or damage that may be caused by the stimulation. For some applications, the stimulation techniques described herein may be used to stimulate sensory receptors (such as coetaneous cold or stretch receptors), in order to activate sensory gateways for chronic pain reduction substantially without inducing pain.

For some applications, stimulation techniques described herein may be used to stimulate a nerve such as the ulnar nerve, in order to cause muscle activity, while minimizing any associated adverse pain, discomfort, or damage that may be caused by the stimulation. For some applications, stimulation techniques described herein may be used to stimulate a sensory nerve, such as the ophthalmic branch of the trigeminal nerve, to induce painless neuromodulation, such as for the treatment of epilepsy, or other disorders treatable by nerve stimulation.

For some applications, stimulation techniques described herein may be used to stimulate skeletal muscles, such as in order to train the muscle, to improve the muscle tone or gait of the subject, or to burn calories, while minimizing any adverse pain, discomfort, or damage that may be caused by such stimulation. For some applications, stimulation techniques described herein may be used to stimulate the detrusor muscle, in order to control urinary symptoms, while minimizing any adverse pain, discomfort, or damage that may be caused by such stimulation.

For some applications, techniques described herein are used to apply controlled stimulation to one or more of the following: the lacrimal nerve, the salivary nerve, the vagus nerve, the pelvic splanchnic nerve, or one or more sympathetic or parasympathetic autonomic nerves. Such controlled stimulation may be applied to such nerves directly, or indirectly, such as by stimulating an adjacent blood vessel or space. Such controlled stimulation may be used, for example, to regulate or treat a condition of the lung, heart, stomach, pancreas, small intestine, liver, spleen, kidney, bladder, rectum, large intestine, reproductive organs, or adrenal gland.

As appropriate, techniques described herein are practiced in conjunction with methods and apparatus described in one or more of the following patent applications, all of which are assigned to the assignee of the present application and are incorporated herein by reference:

U.S. patent application Ser. No. 10/205,474, filed Jul. 24, 2002, entitled, "Electrode assembly for nerve control," which published as US Patent Publication 2003/0050677

U.S. Provisional Patent Application 60/383,157 to Ayal et al., filed May 23, 2002, entitled, "Inverse recruitment for autonomic nerve systems"

U.S. patent application Ser. No. 10/205,475, filed Jul. 24, 2002, entitled, "Selective nerve fiber stimulation for treating heart conditions," which published as US Patent Publication 2003/0045909

PCT Patent Application PCT/IL02/00068, filed Jan. 23, 2002, entitled, "Treatment of disorders by unidirectional nerve stimulation," and U.S. patent application Ser. No. 10/488,334, filed Feb. 27, 2004, in the US National Phase thereof U.S. patent application Ser. No. 09/944,913, filed Aug. 31, 2001, entitled, "Treatment of disorders by unidirectional nerve stimulation"

U.S. patent application Ser. No. 10/461,696, filed Jun. 13, 2003, entitled, "Vagal stimulation for anti-embolic therapy"

PCT Patent Application PCT/IL03/00430, filed May 23, 2003, entitled, "Electrode assembly for nerve control," which published as PCT Publication WO 03/099373

PCT Patent Application PCT/IL03/00431, filed May 23, 2003, entitled, "Selective nerve fiber stimulation for treating heart conditions," which published as PCT Publication WO 03/099377

U.S. patent application Ser. No. 10/719,659, filed Nov. 20, 2003, entitled, "Selective nerve fiber stimulation for treating heart conditions"

PCT Patent Application PCT/IL04/00440, filed May 23, 2004, entitled, "Selective nerve fiber stimulation for treating heart conditions"

PCT Patent Application PCT/IL04/000496, filed Jun. 10, 2004, entitled, "Vagal stimulation for anti-embolic therapy"

U.S. patent application Ser. No. 10/866,601, filed Jun. 10, 2004, entitled, "Applications of vagal stimulation"

PCT Patent Application PCT/IL04/000495, filed Jun. 10, 2004, entitled, "Applications of vagal stimulation"

U.S. patent application Ser. No. 11/022,011, filed Dec. 22, 2004, entitled, "Construction of electrode assembly for nerve control"

U.S. patent application Ser. No. 11/062,324, filed Feb. 18, 2005, entitled, "Techniques for applying, calibrating, and controlling nerve fiber stimulation"

U.S. patent application Ser. No. 11/064,446, filed Feb. 22, 2005, entitled, "Techniques for applying, configuring, and coordinating nerve fiber stimulation"

U.S. patent application Ser. No. 11/280,884, filed Nov. 15, 2005, entitled, "Techniques for nerve stimulation"

U.S. patent application Ser. No. 11/340,156, filed Jan. 25, 2006, entitled, "Method to enhance progenitor or genetically-modified cell therapy"

U.S. patent application Ser. No. 11/359,266, filed Feb. 21, 2006, entitled, "Parasympathetic pacing therapy during and following a medical procedure, clinical trauma or pathology"

It is noted that in many embodiments of the present invention, durations of various stimulation and non-stimulation periods are specified, either as actual values or ranges of actual values, or in relation to durations of other periods. It is to be understood that occasional deviations from such durations during application of stimulation are within the scope of the present invention, so long as on average the parameters of the stimulation meet the specified parameters. "Average," as used herein, including in the claims, is to be understood as meaning an arithmetic mean.

It will be appreciated by persons skilled in the art that current application techniques described herein may be appropriate for application to additional nerves or tissues, such as, for example, cardiac tissue. In addition, techniques described herein may be appropriate for implementation in pacemakers and/or ICDs, mutatis mutandis. For example, techniques described herein for configuring and/or regulating the application of an electrical current may be performed, mutatis mutandis, for applying pacing pulses or anti-arrhythmic energy to the heart.

It will also be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising:
an electrode device, configured to be coupled to a site of a subject;
a sensor, configured to sense a physiological parameter of the subject indicative of cardiac activity of the subject; and
a control unit, configured to:
drive the electrode device to apply to the site a current in at least first and second bursts, the first burst including a plurality of pulses, and the second burst including at least one pulse,
synchronize the first and second bursts with a feature of a cardiac cycle of the subject, and
set (a) a pulse repetition interval (PRI) of the first burst to be on average at least 30 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

2. The apparatus according to claim 1, wherein the control unit is configured to set the percentage to be less than 33%.

3. The apparatus according to claim 1, wherein the control unit is configured to set the average PRI of the first burst to be less than 200 ms.

4. The apparatus according to claim 1, wherein the control unit is configured to set an average duration of the pulses of the first burst to be less than 4 ms.

5. The apparatus according to claim 1, wherein the site is a nerve of the subject, and wherein the electrode device is configured to be coupled to the nerve.

6. The apparatus according to claim 5, wherein the electrode device comprises:
an electrically-insulating cuff, configured to be placed around the nerve; and
electrodes mounted in the cuff.

7. The apparatus according to claim 1, wherein the control unit is configured to:
drive the electrode device to apply the current in at least the first and the second bursts, and in at least a third burst following the second burst, wherein the second burst includes a plurality of pulses, and wherein the third burst includes at least one pulse, and
set (a) a PRI of the second burst to be on average at least 30 ms, (b) an interburst interval between initiation of the second burst and initiation of the third burst to be less than 10 seconds, (c) an interburst gap between a conclusion of the second burst and the initiation of the third burst to have a duration greater than the average PRI of the second burst, and (d) a burst duration of the second burst to be less than 67% of the interburst interval between the initiation of the second burst and initiation of the third burst.

8. The apparatus according to claim 1, wherein the control unit is configured to apply an interburst current to the site during at least a portion of the interburst gap, and to set the interburst current on average to be less than 20% of the current applied on average during the first burst.

9. The apparatus according to claim 1, wherein the control unit is configured to set the average PRI of the first burst to be at least 50 ms.

10. The apparatus according to claim 9, wherein the control unit is configured to set the average PRI of the first burst to be at least 75 ms.

11. The apparatus according to claim 1, wherein the site is selected from the group consisting of: a vagus nerve, an epicardial fat pad, a pulmonary vein, a carotid artery, a carotid sinus, a coronary sinus, a vena cava vein, a right ventricle, a right atrium, and a jugular vein, and wherein the electrode device is configured to be coupled to the selected site.

12. The apparatus according to claim 1, wherein the control unit is configured to synchronize the first and second bursts to commence after a delay after the feature of the cardiac cycle.

13. The apparatus according to claim 12, wherein the feature of the cardiac cycle is selected from the group consisting of: an R-wave of an ECG of the subject, and a P-wave of the ECG.

14. Apparatus comprising:
an electrode device, configured to be coupled to a site of a subject; and a control unit, configured to:
drive the electrode device to apply to the site a current in at least first and second bursts, the first burst including a plurality of pulses, and the second burst including at least one pulse, and
set (a) a pulse repetition interval (PRI) of the first burst to be on average at least 30 ms, (b) an interburst interval between initiation of the first burst and initiation of the second burst to be between 400 ms and 1500 ms, (c) an interburst gap between a conclusion of the first burst and the initiation of the second burst to have a duration greater than the average PRI, and (d) a burst duration of the first burst to be less than a percentage of the interburst interval, the percentage being less than 67%.

15. The apparatus according to claim 14, comprising a sensor configured to sense a physiological parameter of the subject indicative of cardiac activity of the subject, wherein the control unit is configured to synchronize the first and second bursts with a feature of a cardiac cycle of the subject.

16. The apparatus according to claim 14, wherein the site is a nerve of the subject, and wherein the electrode device is configured to be coupled to the nerve.

17. The apparatus according to claim 16, wherein the electrode device comprises:
an electrically-insulating cuff, configured to be placed around the nerve; and
electrodes mounted in the cuff.

18. The apparatus according to claim 14, wherein the control unit is configured to apply an interburst current to the site during at least a portion of the interburst gap, and to set the interburst current on average to be less than 20% of the current applied on average during the first burst.

19. Apparatus comprising:
an electrode device, configured to be coupled to a site of a subject; and
a control unit, configured to:
drive the electrode device to apply to the site a current in at least first and second bursts, the first burst including between two and six pulses, and the second burst including at least one pulse, and
set (a) a pulse repetition interval (PRI) of the first burst to be on average at least 30 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

20. The apparatus according to claim 19 wherein the control unit is configured to configure the first burst to include at least three pulses.

21. The apparatus according to claim 19, wherein the site is a nerve of the subject, and wherein the electrode device is configured to be coupled to the nerve.

22. The apparatus according to claim 21, wherein the electrode device comprises:
an electrically-insulating cuff, configured to be placed around the nerve; and
electrodes mounted in the cuff.

23. The apparatus according to claim 19, wherein the control unit is configured to apply an interburst current to the site during at least a portion of the interburst gap, and to set the interburst current on average to be less than 20% of the current applied on average during the first burst.

24. The apparatus according to claim 19, comprising a sensor configured to sense a physiological parameter of the subject indicative of cardiac activity of the subject, wherein the control unit is configured to synchronize the first and second bursts with a feature of a cardiac cycle of the subject.

25. A method comprising:
coupling an electrode device to a site of a subject selected from the group consisting of: a vagus nerve, an epicardial fat pad, a pulmonary vein, a carotid artery, a carotid sinus, a coronary sinus, a vena cava vein, a right ventricle, a right atrium, and a jugular vein;
using the electrode device, applying, to the site, a current in at least first and second bursts, the first burst including a plurality of pulses, and the second burst including at least one pulse; and
setting (a) a pulse repetition interval (PRI) of the first burst to be on average at least 30 ms, (b) an interburst interval between initiation of the first burst and initiation of the second burst to be less than 10 seconds, (c) an interburst gap between a conclusion of the first burst and the initiation of the second burst to have a duration greater than the average PRI, and (d) a burst duration of the first burst to be less than a percentage of the interburst interval, the percentage being less than 67%.

26. The method according to claim 25, wherein setting comprises setting the percentage to be less than 33%.

27. The method according to claim 25, wherein setting comprises setting the average PRI of the first burst to be less than 200 ms.

28. The method according to claim 25, wherein setting comprises setting the interburst interval to be between 400 ms and 1500 ms.

29. The method according to claim 25, wherein applying comprises configuring the first burst to include at least three pulses.

30. The method according to claim 25, wherein applying the current comprises setting the first burst to include no more than six pulses.

31. The method according to claim 25, wherein applying the current comprises setting an average duration of the pulses of the first burst to be less than 4 ms.

32. The method according to claim 25, wherein the site includes the vagus nerve, and wherein applying the current comprises applying the current to the vagus nerve.

33. The method according to claim 25,
wherein applying comprises applying the current in at least the first and the second bursts, and in at least a third burst following the second burst, wherein the second burst includes a plurality of pulses, and wherein the third burst includes at least one pulse, and
wherein setting comprises setting (a) a PRI of the second burst to be on average at least 30 ms, (b) an interburst interval between initiation of the second burst and initiation of the third burst to be less than 10 seconds, (c) an interburst gap between a conclusion of the second burst and the initiation of the third burst to have a duration greater than the average PRI of the second burst, and (d) a burst duration of the second burst to be less than 67% of the interburst interval between the initiation of the second burst and initiation of the third burst.

34. The method according to claim 25, wherein applying the current comprises applying an interburst current to the site during at least a portion of the interburst gap, and setting the interburst current on average to be less than 20% of the current applied on average during the first burst.

35. The method according to claim 25, wherein setting comprises setting the average PRI of the first burst to be at least 50 ms.

36. The method according to claim 35, wherein setting comprises setting the average PRI of the first burst to be at least 75 ms.

37. The method according to claim 25, wherein applying the current comprises sensing a physiological parameter of the subject indicative of cardiac activity of the subject, and synchronizing the first and second bursts with a feature of a cardiac cycle of the subject.

38. The method according to claim 37, wherein synchronizing comprises synchronizing the first and second bursts to commence after a delay after the feature of the cardiac cycle.

39. The method according to claim 37, wherein the feature of the cardiac cycle is selected from the group consisting of: an R-wave of an ECG of the subject, and a P-wave of the ECG, and wherein synchronizing comprises synchronizing the first and second bursts to commence after the delay after the selected feature of the cardiac cycle.

* * * * *